(12) United States Patent
Li et al.

(10) Patent No.: US 9,711,742 B2
(45) Date of Patent: *Jul. 18, 2017

(54) FOUR COORDINATED PLATINUM AND PALLADIUM COMPLEXES WITH GEOMETRICALLY DISTORTED CHARGE TRANSFER STATE AND THEIR APPLICATIONS IN LIGHT EMITTING DEVICES

(71) Applicant: Arizona Board of Regents Acting for and on Behalf of Arizona State University, Scottsdale, AZ (US)

(72) Inventors: Jian Li, Tempe, AZ (US); Eric Turner, Scottsdale, AZ (US); Xiaochun Hang, Scottsdale, AZ (US)

(73) Assignee: ARIZONA BOARD OF REGENTS ACTING FOR AND ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/243,801

(22) Filed: Aug. 22, 2016

(65) Prior Publication Data
US 2017/0047533 A1 Feb. 16, 2017

Related U.S. Application Data

(62) Division of application No. 14/589,599, filed on Jan. 5, 2015, now Pat. No. 9,425,415, which is a division of application No. 14/332,610, filed on Jul. 16, 2014, now Pat. No. 8,927,713, which is a division of application No. 13/399,252, filed on Feb. 17, 2012, now Pat. No. 8,816,080.

(60) Provisional application No. 61/444,387, filed on Feb. 18, 2011.

(51) Int. Cl.
| C07F 15/00 | (2006.01) |
| H01L 51/50 | (2006.01) |
| H01L 51/00 | (2006.01) |
| C09K 11/06 | (2006.01) |
| H01L 51/44 | (2006.01) |
| H01L 51/52 | (2006.01) |

(52) U.S. Cl.
CPC ...... H01L 51/0087 (2013.01); C07F 15/0086 (2013.01); C09K 11/06 (2013.01); *C09K 2211/1003* (2013.01); *C09K 2211/1007* (2013.01); *C09K 2211/1014* (2013.01); *C09K 2211/1044* (2013.01); *C09K 2211/185* (2013.01); *H01L 51/44* (2013.01); *H01L 51/5016* (2013.01); *H01L 51/5072* (2013.01); *H01L 51/5234* (2013.01)

(58) Field of Classification Search
CPC ............... C07F 15/00; H01L 51/50

USPC ........................... 546/10; 313/504
See application file for complete search history.

(56) References Cited

U.S. PATENT DOCUMENTS

| | | |
|---|---|---|
| 4,769,292 A | 9/1988 | Tang et al. |
| 5,707,745 A | 1/1998 | Forrest et al. |
| 5,844,363 A | 12/1998 | Gu et al. |
| 6,303,238 B1 | 10/2001 | Thompson et al. |
| 6,780,528 B2 | 8/2004 | Tsuboyama et al. |
| 7,002,013 B1 | 2/2006 | Chi et al. |
| 7,037,599 B2 | 5/2006 | Culligan et al. |
| 7,279,704 B2 | 10/2007 | Walters et al. |
| 7,332,232 B2 | 2/2008 | Ma et al. |
| 7,442,797 B2 | 10/2008 | Itoh et al. |
| 7,501,190 B2 | 3/2009 | Ise |
| 7,655,322 B2 | 2/2010 | Forrest et al. |
| 7,947,383 B2 | 5/2011 | Ise et al. |
| 8,389,725 B2 | 3/2013 | Li et al. |
| 8,617,723 B2 | 12/2013 | Stoessel |
| 8,816,080 B2 | 8/2014 | Li et al. |
| 8,871,361 B2 | 10/2014 | Xia et al. |
| 8,927,713 B2 | 1/2015 | Li et al. |
| 8,946,417 B2 | 2/2015 | Jian et al. |
| 9,059,412 B2 | 6/2015 | Zeng et al. |
| 9,224,963 B2 | 12/2015 | Li et al. |
| 9,238,668 B2 | 1/2016 | Li et al. |
| 9,312,505 B2 | 4/2016 | Brooks et al. |
| 9,324,957 B2 | 4/2016 | Li et al. |
| 9,382,273 B2 | 7/2016 | Li |
| 9,385,329 B2 | 7/2016 | Li et al. |
| 9,425,415 B2 | 8/2016 | Li et al. |
| 9,550,801 B2 | 1/2017 | Li et al. |
| 2002/0068190 A1 | 6/2002 | Tsuboyama et al. |
| 2003/0062519 A1 | 4/2003 | Yamazaki et al. |
| 2005/0170207 A1 | 8/2005 | Ma et al. |
| 2005/0260446 A1 | 11/2005 | Mackenzie et al. |
| 2006/0073359 A1 | 4/2006 | Ise et al. |
| 2006/0094875 A1 | 5/2006 | Itoh et al. |
| 2006/0202197 A1 | 9/2006 | Nakayama et al. |
| 2006/0210831 A1 | 9/2006 | Sano et al. |
| 2006/0263635 A1 | 11/2006 | Ise |
| 2006/0286406 A1 | 12/2006 | Igarashi et al. |
| 2007/0057630 A1 | 3/2007 | Nishita et al. |
| 2007/0059551 A1 | 3/2007 | Yamazaki |
| 2007/0082284 A1 | 4/2007 | Stoessel et al. |
| 2007/0103060 A1 | 5/2007 | Itoh et al. |

(Continued)

FOREIGN PATENT DOCUMENTS

| CN | 1777663 | 5/2006 |
| CN | 1894269 | 1/2007 |

(Continued)

OTHER PUBLICATIONS

Marc Lepeltier et al., "Efficient blue green organic light-emitting devices based on a monofluorinated heteroleptic ridium(III) complex," Synthetic Metals, vol. 199, 2015, pp. 139-146.

(Continued)

*Primary Examiner* — Charanjit Aulakh
(74) *Attorney, Agent, or Firm* — Fish & Richardson P.C.

(57) ABSTRACT

Described herein are platinum and palladium compounds with geometrically distorted charge transfer state, applications and methods for the preparation thereof. The platinum and/or palladium compounds described herein are capable of emitting light and can be used in light emitting devices.

17 Claims, 6 Drawing Sheets

(56) References Cited

U.S. PATENT DOCUMENTS

| | | |
|---|---|---|
| 2008/0001530 A1 | 1/2008 | Ise et al. |
| 2008/0036373 A1 | 2/2008 | Itoh et al. |
| 2008/0054799 A1 | 3/2008 | Satou |
| 2008/0079358 A1 | 4/2008 | Satou |
| 2008/0241518 A1 | 10/2008 | Satou et al. |
| 2008/0241589 A1 | 10/2008 | Fukunaga et al. |
| 2009/0026936 A1 | 1/2009 | Satou et al. |
| 2009/0026939 A1 | 1/2009 | Kinoshita et al. |
| 2009/0032989 A1 | 2/2009 | Karim et al. |
| 2009/0039768 A1 | 2/2009 | Igarashi et al. |
| 2009/0079340 A1 | 3/2009 | Kinoshita et al. |
| 2009/0128008 A1 | 5/2009 | Ise et al. |
| 2009/0218561 A1 | 9/2009 | Kitamura et al. |
| 2009/0261721 A1 | 10/2009 | Murakami et al. |
| 2009/0267500 A1 | 10/2009 | Kinoshita et al. |
| 2010/0000606 A1 | 1/2010 | Thompson et al. |
| 2010/0013386 A1 | 1/2010 | Thompson et al. |
| 2010/0171111 A1 | 7/2010 | Takada et al. |
| 2012/0095232 A1 | 4/2012 | Li et al. |
| 2012/0181528 A1 | 7/2012 | Takada et al. |
| 2012/0215001 A1 | 8/2012 | Li et al. |
| 2012/0223634 A1 | 9/2012 | Xia et al. |
| 2012/0302753 A1 | 11/2012 | Li |
| 2013/0048963 A1 | 2/2013 | Beers et al. |
| 2013/0168656 A1 | 7/2013 | Tsai et al. |
| 2013/0203996 A1 | 8/2013 | Li et al. |
| 2013/0237706 A1 | 9/2013 | Li |
| 2013/0341600 A1 | 12/2013 | Lin et al. |
| 2014/0014922 A1 | 1/2014 | Lin et al. |
| 2014/0027733 A1 | 1/2014 | Zeng et al. |
| 2014/0084261 A1 | 3/2014 | Brooks et al. |
| 2014/0114072 A1 | 4/2014 | Li et al. |
| 2014/0203248 A1 | 7/2014 | Zhou et al. |
| 2014/0330019 A1 | 11/2014 | Li et al. |
| 2014/0364605 A1 | 12/2014 | Li et al. |
| 2015/0008419 A1 | 1/2015 | Li |
| 2015/0028323 A1 | 1/2015 | Xia et al. |
| 2015/0069334 A1 | 3/2015 | Xia et al. |
| 2015/0105556 A1 | 4/2015 | Li et al. |
| 2015/0162552 A1 | 6/2015 | Li et al. |
| 2015/0194616 A1 | 7/2015 | Li et al. |
| 2015/0228914 A1 | 8/2015 | Li et al. |
| 2015/0287938 A1 | 10/2015 | Li et al. |
| 2015/0318500 A1 | 11/2015 | Li |
| 2015/0349279 A1 | 12/2015 | Li et al. |
| 2016/0028028 A1 | 1/2016 | Li et al. |
| 2016/0043331 A1 | 2/2016 | Li et al. |
| 2016/0072082 A1 | 3/2016 | Brooks et al. |
| 2016/0133862 A1 | 5/2016 | Li et al. |
| 2016/0197291 A1 | 7/2016 | Li et al. |
| 2016/0285015 A1 | 9/2016 | Li et al. |
| 2016/0359120 A1 | 12/2016 | Li |
| 2016/0359125 A1 | 12/2016 | Li et al. |
| 2017/0005278 A1 | 1/2017 | Li et al. |
| 2017/0012224 A1 | 1/2017 | Li et al. |

FOREIGN PATENT DOCUMENTS

| | | |
|---|---|---|
| CN | 101142223 | 3/2008 |
| CN | 101667626 | 3/2010 |
| CN | 102449108 A | 5/2012 |
| CN | 102892860 | 1/2013 |
| CN | 102971396 | 3/2013 |
| CN | 104232076 | 12/2014 |
| CN | 104693243 | 6/2015 |
| CN | 105367605 | 3/2016 |
| CN | 105418591 | 3/2016 |
| EP | 1808052 | 7/2007 |
| EP | 1874893 | 1/2008 |
| EP | 1874894 | 1/2008 |
| EP | 1919928 | 5/2008 |
| EP | 2036907 | 3/2009 |
| EP | 2096690 A2 | 9/2009 |
| EP | 2417217 | 2/2012 |
| EP | 2112213 | 7/2012 |
| EP | 2711999 | 3/2014 |
| JP | 2005267557 | 9/2005 |
| JP | 2005310733 | 11/2005 |
| JP | 2006047240 | 2/2006 |
| JP | 2006232784 | 9/2006 |
| JP | 2006242080 | 9/2006 |
| JP | 2006242081 | 9/2006 |
| JP | 2006256999 | 9/2006 |
| JP | 2006257238 | 9/2006 |
| JP | 2006261623 | 9/2006 |
| JP | 2006290988 | 10/2006 |
| JP | 2006313796 | 11/2006 |
| JP | 2006332622 | 12/2006 |
| JP | 2006351638 | 12/2006 |
| JP | 2007019462 | 1/2007 |
| JP | 2007042875 | 2/2007 |
| JP | 2007053132 | 3/2007 |
| JP | 2007066581 | 3/2007 |
| JP | 2007073620 | 3/2007 |
| JP | 2007073845 | 3/2007 |
| JP | 2007073900 | 3/2007 |
| JP | 2007080593 | 3/2007 |
| JP | 2007080677 | 3/2007 |
| JP | 2007088105 | 4/2007 |
| JP | 2007088164 | 4/2007 |
| JP | 2007096259 | 4/2007 |
| JP | 2007110067 | 4/2007 |
| JP | 2007110102 | 4/2007 |
| JP | 2007258550 | 10/2007 |
| JP | 2007324309 | 12/2007 |
| JP | 2008010353 | 1/2008 |
| JP | 2008091860 | 4/2008 |
| JP | 2008103535 | 5/2008 |
| JP | 2008108617 | 5/2008 |
| JP | 2008109085 | 5/2008 |
| JP | 2008109103 | 5/2008 |
| JP | 2008160087 | 7/2008 |
| JP | 2008198801 | 8/2008 |
| JP | 2008270729 | 11/2008 |
| JP | 2008270736 | 11/2008 |
| JP | 2009016184 | 1/2009 |
| JP | 2009016579 | 1/2009 |
| JP | 2009032977 | 2/2009 |
| JP | 2009032988 | 2/2009 |
| JP | 2009266943 | 11/2009 |
| JP | 2009267171 | 11/2009 |
| JP | 2009267244 | 11/2009 |
| JP | 2009272339 | 11/2009 |
| JP | 2009283891 | 12/2009 |
| JP | 2010135689 | 6/2010 |
| JP | 2012222255 | 11/2012 |
| JP | 2013525436 | 6/2013 |
| JP | 5604505 | 10/2014 |
| JP | 2014221807 | 11/2014 |
| JP | 2015081257 | 4/2015 |
| KR | 1020060115371 | 11/2006 |
| KR | 2007061830 | 6/2007 |
| KR | 2007112465 | 11/2007 |
| KR | 1020130043460 | 4/2013 |
| TW | 200701835 | 1/2007 |
| TW | 201307365 | 2/2013 |
| WO | WO0070655 | 11/2000 |
| WO | WO2004003108 A1 | 1/2004 |
| WO | WO2004108857 | 12/2004 |
| WO | WO2005042444 | 5/2005 |
| WO | WO2005042550 | 5/2005 |
| WO | WO2006033440 | 3/2006 |
| WO | WO2006098505 | 9/2006 |
| WO | WO2006115299 | 11/2006 |
| WO | WO2006115301 | 11/2006 |
| WO | WO2007034985 | 3/2007 |
| WO | WO2007069498 | 6/2007 |
| WO | WO2008066192 | 6/2008 |
| WO | WO2008066195 | 6/2008 |
| WO | WO2008066196 | 6/2008 |
| WO | WO2008117889 | 10/2008 |
| WO | WO2008123540 | 10/2008 |
| WO | WO2009017211 | 2/2009 |
| WO | WO2010118026 | 10/2010 |

(56) References Cited

FOREIGN PATENT DOCUMENTS

| WO | WO2011137429 | 11/2011 |
|---|---|---|
| WO | WO2011137431 | 11/2011 |
| WO | WO2012112853 | 8/2012 |
| WO | WO2012142387 | 10/2012 |
| WO | WO2012162488 | 11/2012 |
| WO | WO2012163471 | 12/2012 |
| WO | WO2013130483 | 9/2013 |
| WO | WO2014031977 | 2/2014 |
| WO | WO2014047616 | 3/2014 |
| WO | WO2014016611 A1 | 4/2014 |
| WO | WO2014109814 | 7/2014 |
| WO | WO2015027060 | 2/2015 |
| WO | WO2015131158 | 9/2015 |
| WO | WO2016025921 | 2/2016 |
| WO | WO2016029186 | 2/2016 |

OTHER PUBLICATIONS

Stefan Bernhard, "The First Six Years: A Report," Department of Chemistry, Princeton University, May 2008, 11 pages.

International Search Report issued on Jun. 5, 2012 for Intl. App. No. PCT/US2012/025588, filed Feb. 17, 2012 (Inventor—Li et al.; Applicant—Arizona Board of Regents acting for and on behalf of Arizona State University; pp. 1-3).

International Preliminary Report on Patentability issued on Aug. 21, 2013 for Intl. App. No. PCT/US2012/025588, filed Feb. 17, 2012 and published as WO 2012/112853 on Aug. 23, 2012 (Applicants—Arizona Board of Regents acting for and on behalf of Arizona State University; Inventors—Li et al.; (5 pages).

Written Opinion mailed on Jun. 5, 2012 for Intl. App. No. PCT/US2012/025588, filed Feb. 17, 2012 and published as WO 2012/112853 on Aug. 23, 2012 (Applicants—Arizona Board of Regents acting for and on behalf of Arizona State University; Inventors—Li et al.; (4 pages).

Office Action and Search Report (and English Translation) for Taiwan Patent Application No. 101105333, issued Jun. 26, 2015, 9 pages.

Wong; Challenges in organometallic research—Great opportunity for solar cells and OLEDs, Journal of Organometallic Chemistry, 2009, 694, 2644-2647.

JP2009267244, English Translation from EPO, Nov. 2009, 80 pages.

JP2010135689, English translation from EPO, Jun. 2010, 95 pages.

Chi et al.; Transition-metal phosphors with cyclometalating ligands: fundamentals and applications, Chemical Society Reviews, vol. 39, No. 2, Feb. 2010, pp. 638-655.

Satake et al., "Interconvertible Cationic and Neutral Pyridinylimidazole η3-Allylpalladium Complexes. Structural Assignment by 1H, 13C, and 15N NMR and X-ray Diffraction", Organometallics, vol. 18, No. 24, 1999, pp. 5108-5111.

Baldo et al., "Highly Efficient Phosphorescent Emission from Organic Electroluminescent Devices," Nature, vol. 395, Sep. 10, 1998, pp. 151-154.

Baldo et al., "Very high-efficiency green organic light-emitting devices based on electrophosphorescence," Applied Physics Letters, vol. 75, No. 1, Jul. 5, 1999, pp. 4-6.

Ji Hyun Seo et al., "Efficient blue-green organic light-emitting diodes based on heteroleptic tris-cyclometalated iridium (III) complexes". Thin Solid Films, vol. 517, pp. 1807-1810 (2009).

Vanessa Wood et al., "Colloidal quantum dot light-emitting devices," Nano Reviews, vol. 1, 2010, 8 pages.

Glauco Ponterini et al., "Comparison of Radiationless Decay Processes in Osmium and Platinum Porphyrins," J. Am. Chem. Soc., vol. 105, No. 14, 1983, pp. 4639-4645.

Shizuo Tokito et al., "Confinement of triplet energy on phosphorescent molecules for highly-efficient organic blue-light-emitting devices," Applied Physics Letters, vol. 83, No. 3, Jul. 21, 2003, pp. 569-571.

Brian W. D'Andrade et al., "Controlling Exciton Diffusion in Multilayer White Phosphorescent Organic Light Emitting Devices," Adv. Mater., vol. 14, No. 2, Jan. 16, 2002, pp. 147-151.

Dileep A. K. Vezzu et al., "Highly Luminescent Tetradentate Bis-Cyclometalated Platinum Complexes: Design, Synthesis, Structure, Photophysics, and Electroluminescence Application," Inorg. Chem., vol. 49, 2010, pp. 5107-5119.

Evan L. Williams et al., "Excimer-Based White Phosphorescent Organic Light Emitting Diodes with Nearly 100% Internal Quantum Efficiency," Adv. Mater., vol. 19, 2007, pp. 197-202.

Shih-Chun Lo et al., "High-Triplet-Energy Dendrons: Enhancing the Luminescence of Deep Blue Phosphorescent Iridium(III) Complexes," J. Am. Chem. Soc., vol. 131, 2009, pp. 16681-16688.

Jan Kalinowski et al., "Light-emitting devices based on organometallic platinum complexes as emitters," Coordination Chemistry Reviews, vol. 255, 2011, pp. 2401-2425.

Ke Feng et al., "Norbornene-Based Copolymers Containing Platinum Complexes and Bis(carbazolyl)benzene Groups in Their Side-Chains," Macromolecules, vol. 42, 2009, pp. 6855-6864.

Chi-Ming Che et al., "Photophysical Properties and OLED Applications of Phosphorescent Platinum(II) Schiff Base Complexes," Chem. Eur. J., vol. 16, 2010, pp. 233-247.

Stephen R. Forrest, "The path to ubiquitous and low-cost organic electronic appliances on plastic," Nature, vol. 428, Apr. 29, 2004, pp. 911-918.

Nicholas R. Evans et al., "Triplet Energy Back Transfer in Conjugated Polymers with Pendant Phosphorescent Iridium Complexes," J. Am. Chem. Soc., vol. 128, 2006, pp. 6647-6656.

Xiaofan Ren et al., "Ultrahigh Energy Gap Hosts in Deep Blue Organic Electrophosphorescent Devices," Chem. Mater., vol. 16, 2004, pp. 4743-4747.

Jeonghun Kwak et al., "Bright and Efficient Full-Color Colloidal Quantum Dot Light-Emitting Diodes Using an Inverted Device Structure," Nano Lett., 2012, Vo. 12, pp. 2362-2366.

Hirohiko Fukagawa et al., "Highly Efficient and Stable Red Phosphorescent Organic Light-Emitting Diodes Using Platinum Complexes," Adv. Mater., 2012, vol. 24, pp. 5099-5103.

Dorwald; "Side Reactions in Organic Synthesis: A Guide to Successful Synthesis Design," Chapter 1, 2005 Wiley-VCH Verlag GmbH & Co. KGaA, Wienheim, 32 pages.

Murakami; JP 2007258550, English machine translation from EPO, Oct. 4, 2007. 80 pages.

Murakami; JP 2007324309, English machine translation from EPO, Dec. 13, 2007, 89 pages.

FOUR COORDINATED PLATINUM AND PALLADIUM COMPLEXES WITH GEOMETRICALLY DISTORTED CHARGE TRANSFER STATE AND THEIR APPLICATIONS IN LIGHT EMITTING DEVICES

CROSS REFERENCE TO RELATED APPLICATIONS

This application is a divisional of U.S. patent application Ser. No. 14/589,599, filed on Jan. 5, 2015, now allowed, which is a divisional of U.S. patent application Ser. No. 14/332,610, filed on Jul. 16, 2014, now U.S. Pat. No. 8,927,713, which is a divisional of U.S. patent application Ser. No. 13/399,252, filed on Feb. 17, 2012, now U.S. Pat. No. 8,927,713, which claims priority to U.S. Provisional Patent Application No. 61/444,387, filed on Feb. 18, 2011, all of which are hereby incorporated by reference in their entirety.

TECHNICAL FIELD

The present disclosure relates to platinum and/or palladium complexes which are capable of emitting light and are thus useful as an emissive material in a device.

TECHNICAL BACKGROUND

Compounds capable of absorbing and/or emitting light are ideally suited for use in a wide variety of optical and electro-optical devices, including photo-absorbing devices such as solar- and photo-sensitive devices, photo-emitting devices, such as organic light emitting diodes (OLEDs), or devices capable of both photo-absorption and emission. Much research has been devoted to the discovery and optimization of organic and organometallic materials for use in optical and electro-optical devices. Generally, research in this area aims to accomplish a number of goals, including improvements in absorption and emission efficiency, as well as improvements in processing ability, among others.

Despite significant advances in research devoted to optical and electro-optical materials, many current devices comprising organic or organometallic materials have yet to be optimized. Many materials currently used in optical and electro-optical devices have a number of disadvantages, including poor processing ability, inefficient emission or absorption, and less than ideal stability, among others. Thus, a need exists for new materials which exhibit improved performance in optical and electro-optical devices. This need and other needs are satisfied by the present invention.

SUMMARY

The present invention relates to platinum, palladium or combination thereof complexes that exhibit photoemission, to methods of making such compounds, and to applications thereof, including optical devices comprising the compounds.

In one aspect, the compounds are represented by the formula:

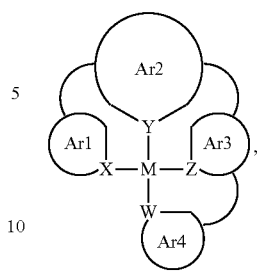

wherein each of Ar1, Ar2, Ar3, and Ar4 comprise an aromatic ring or heterocyclic group comprising an atom X, Y, Z and W, respectively, coordinating to M atom by a linkage group, wherein each of the linkage groups comprise a carbon, nitrogen, halogen, sulfur, phosphor, oxygen, or a combination thereof, and wherein M atom is platinum, palladium or combination thereof.

In another aspect, the present disclosure provides a compound represented by the formula

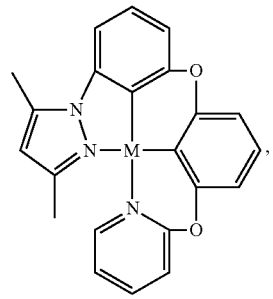

wherein M is atom of platinum, palladium or combination thereof.

In another aspect, the present disclosure provides a compound represented by the formula

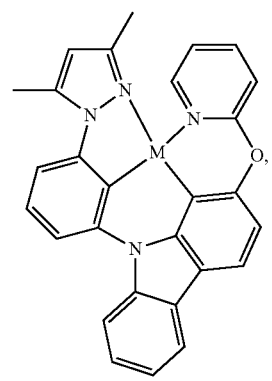

wherein M is atom of platinum, palladium or combination thereof.

In another aspect, the present disclosure provides a compound represented by the formula

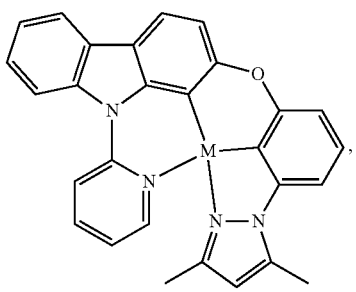

wherein M is atom of platinum, palladium or combination thereof.

In other aspects, the present disclosure provides a light emitting device comprising at least one of the compounds described herein.

Also disclosed are optical devices, such as organic light emitting devices, photovoltaic devices (e.g., solar cells), and luminescent display devices that comprise one or more compounds of the invention as a functional material, such as a light-emitter or absorber, or both.

BRIEF DESCRIPTION OF THE FIGURES

The accompanying figures, which are incorporated in and constitute a part of this specification, illustrate several aspects and together with the description serve to explain the principles of the invention.

Figure 1A:
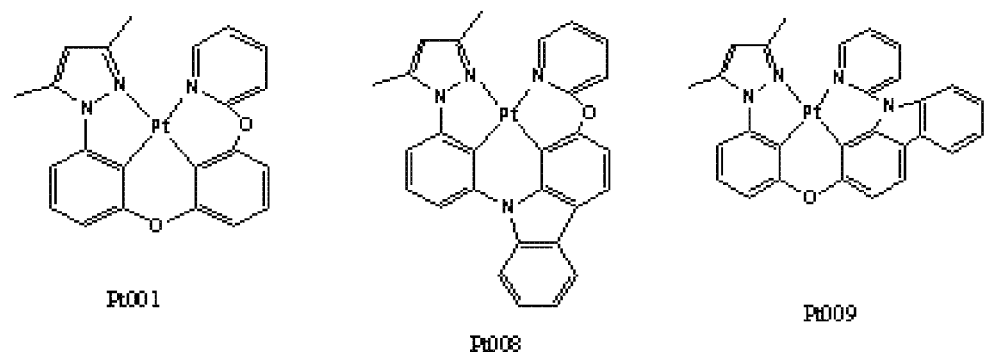
FIG. 1A illustrates chemical structures for Pt-001, Pt-008, and Pt-009 complexes, in accordance with various aspects of the present disclosure.
Figure 1B:
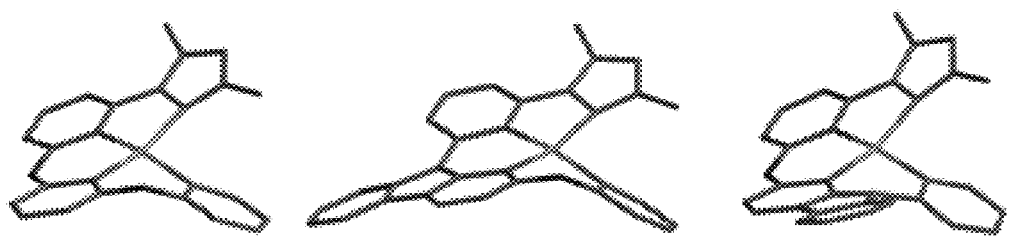
FIG. 1B illustrates DFT drawings of Pt-001 (left), Pt-008 (center), and Pt-009 (right) structures, in accordance with various aspects of the present disclosure.
Figure 1C:
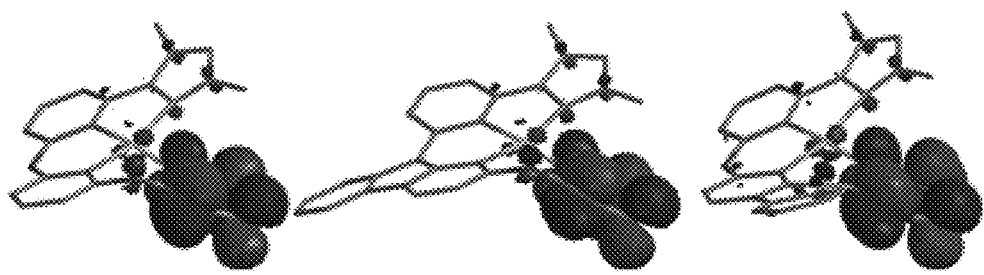
FIG. 1C depicts structure drawings illustrating the lowest unoccupied molecular orbital (LUMO) for each of Pt-001 (left), Pt-008 (center), and Pt-009 (right), in accordance with various aspects of the present disclosure.
Figure 1D:
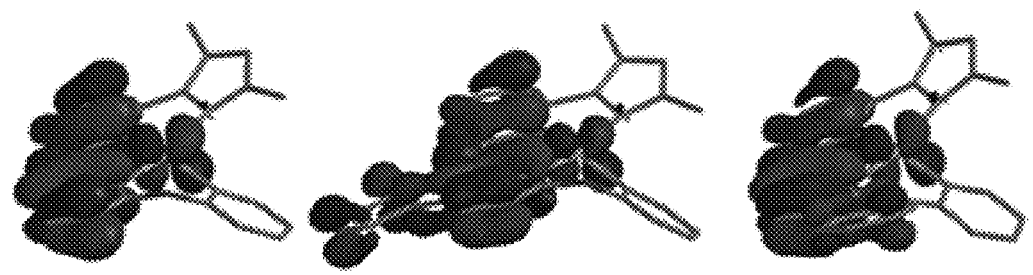
FIG. 1D depicts structure drawings illustrating the highest occupied molecular orbital (HOMO) for each of Pt-001 (left), Pt-008 (center), and Pt-009 (right), in accordance with various aspects of the present disclosure.
Figure 2A:
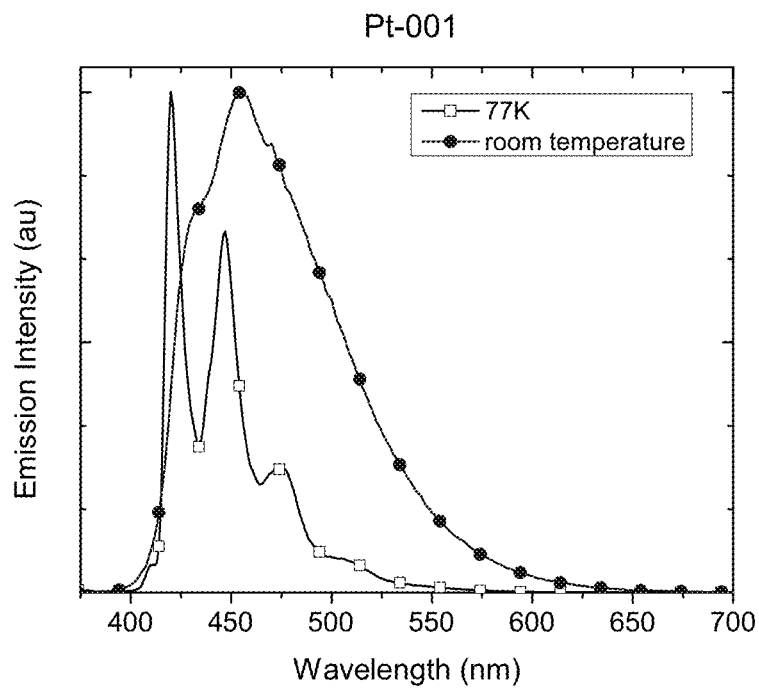
FIG. 2A illustrates the room temperature and 77K emission spectra of a Pt-001 complex, in accordance with various aspects of the present disclosure.
Figure 2B:
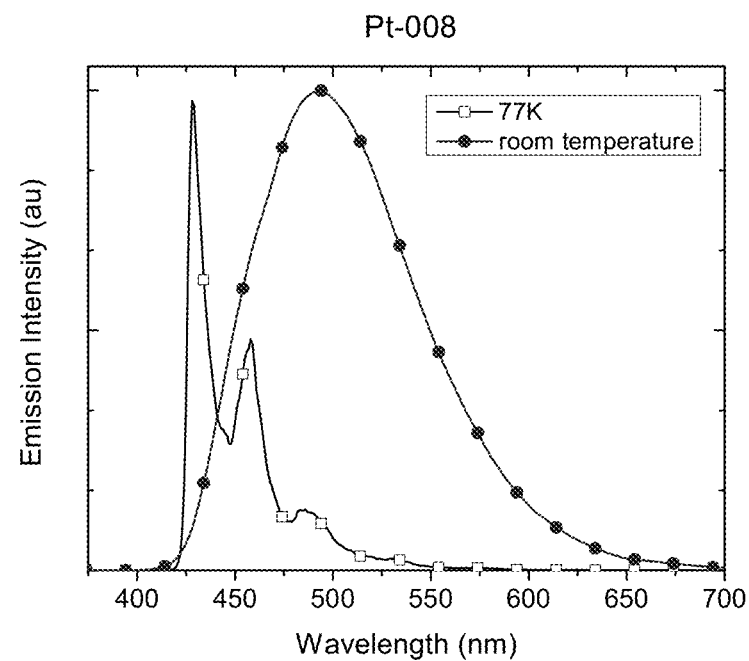
FIG. 2B illustrates the room temperature and 77K emission spectra of a Pt-008 complex, in accordance with various aspects of the present disclosure.
Figure 2C:
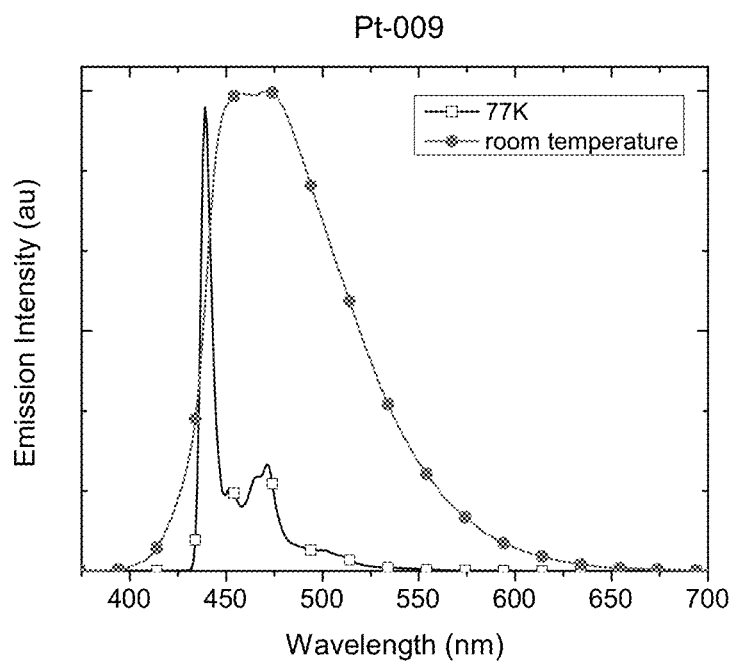
FIG. 2C illustrates the room temperature and 77K emission spectra of a Pt-009 complex, in accordance with various aspects of the present disclosure.
Figure 3A:
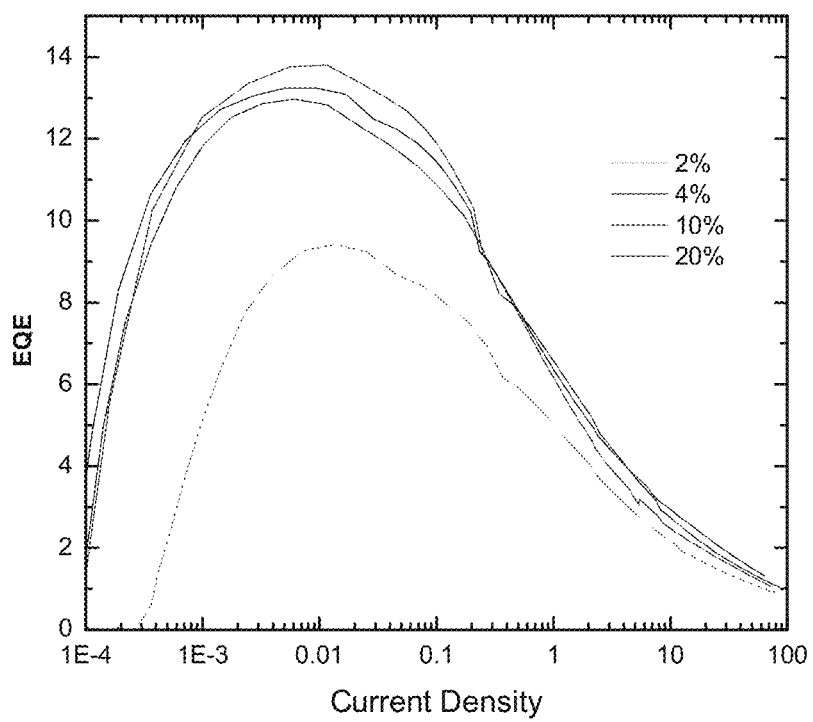
FIG. 3A is a plot of device efficiency vs. current density for an ITO/PEDOT:PSS/NPD (30 nm)/TAPC (10 nm)/Pt-008:mCpy (25 nm)/PO15 (20 nm)/LiF/Al device for Pt-008 ranging from 2 to 20%).
Figure 3B:
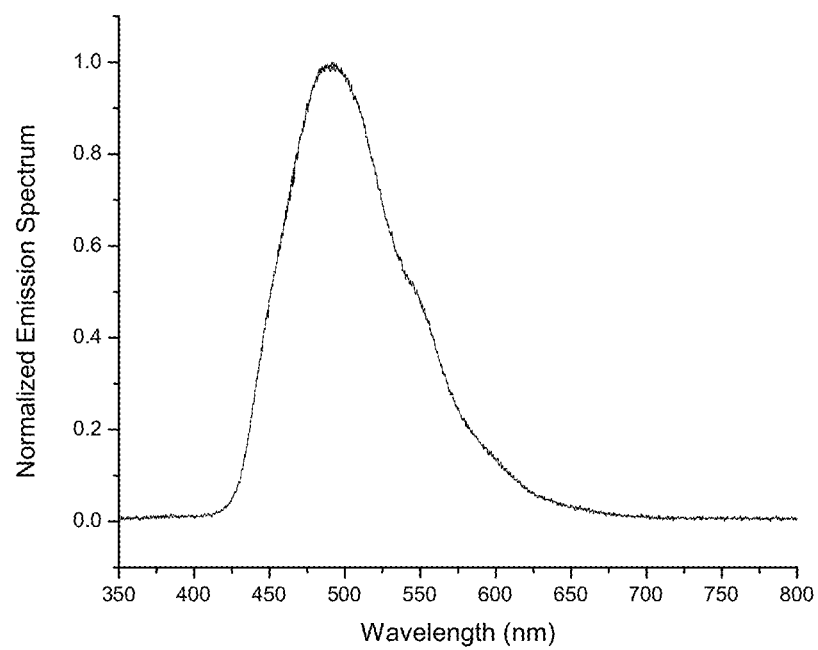
FIG. 3B illustrates the electroluminescent spectrum for an ITO/PEDOT:PSS/NPD (30 nm)/TAPC (10 nm)/Pt-008 (4%):mCPy (25 nm)/PO15 (20 nm)/LiF/Al device.

Additional aspects of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, devices, and/or methods are disclosed and described, it is to be understood that they are not limited to specific synthetic methods unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

As used in the specification and the appended claims, the singular forms "a," "an" and "the" include plural referents unless the context clearly dictates otherwise. Thus, for example, reference to "a component" includes mixtures of two or more components.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or cannot occur, and that the description includes instances where said event or circumstance occurs and instances where it does not.

It is also to be understood that if not described otherwise or specifically excluded all Pt atoms in the description of the inventive compounds can be substituted by Pd, or combination of Pt—Pd atoms.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

The terms "amine" or "amino" as used herein are represented by the formula $NA^1A^2A^3$, where $A^1$, $A^2$, and $A^3$ can be, independently, hydrogen or optionally substituted alkyl, cycloalkyl, alkenyl, cycloalkenyl, alkynyl, cycloalkynyl, aryl, or heteroaryl group as described herein.

The term "halide" as used herein refers to the halogens fluorine, chlorine, bromine, and iodine.

The term "hydroxyl" as used herein is represented by the formula —OH.

The term "nitro" as used herein is represented by the formula $—NO_2$.

The term "nitrile" as used herein is represented by the formula —CN.

The term "thiol" as used herein is represented by the formula —SH.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

In one aspect, the present application discloses platinum and/or palladium complexes that can emit electromagnetic radiation. In another aspect, the emission of such inventive complexes can be tuned, for example, from the ultraviolet to near-infrared, by, for example, modifying the ligand structure. In another aspect, the inventive complexes can provide emission over a majority of the visible spectrum. In a specific example, the inventive complexes can emit light over a range of from about 400 nm to about 700 nm. In another aspect, the inventive complexes have improved stability and efficiency over traditional emission complexes. In yet another aspect, the inventive complexes can be useful as luminescent labels in, for example, bio-applications, anti-cancer agents, emitters in organic light emitting diodes (OLED), or a combination thereof. In another aspect, the inventive complexes can be useful in light emitting devices, such as, for example, compact fluorescent lamps (CFL), light emitting diodes (LED), incandescent lamps, and combinations thereof.

In one aspect, the inventive complex comprises a metal atom and a ligand. In another aspect, the ligand is a tridentate ligand and is attached to the metal atom with three ligands of the same or varying composition. In another aspect, the ligand is a tetradentate ligand. In another aspect, the metal atom comprises at least one of platinum, palladium, or an alloy or combination thereof. In one aspect, the metal atom is platinum. In another aspect, the metal atom is palladium.

In one aspect, the ligand comprises one or more of the following: a high triplet energy emitting ligand having a rigid structure, a donor-acceptor ligand having a distorted geometry, or a combination thereof. In one aspect, the complex comprises a high triplet energy emitting ligand having a rigid structure and a donor-acceptor ligand with a distorted geometry. In another aspect, any one or more ligands can be connected through a bridging ligand. The specific ligand, structure, and/or bridging ligand can vary as described herein, and one of skill in the art, in possession of this disclosure, could readily select appropriate ligands for a platinum and/or palladium complex.

In one aspect, the inventive complexes of the present disclosure can be represented by the general formula:

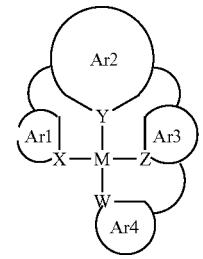

wherein each of Ar1, Ar2, Ar3, and Ar4 comprise an aromatic ring or heterocyclic group comprising an atom X, Y, Z and W, respectively, coordinating to a M atom by a linkage group, wherein each of the linkage groups comprise a carbon, nitrogen, halogen, sulfur, phosphor, oxygen, or a combination thereof, which can, in various aspects, be substituted and/or connected with each other, and wherein the M atom can comprise platinum, palladium or combination thereof.

In one aspect, the inventive complex an emitting component, such as, for example,

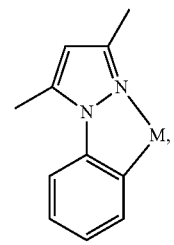

wherein M is atom of platinum, palladium or combination thereof.

In various aspects, the inventive complex can comprise the emitting component illustrated above, and a same or different donor-acceptor component. In one such aspect, the emitting component and the donor-acceptor component can form the following structure:

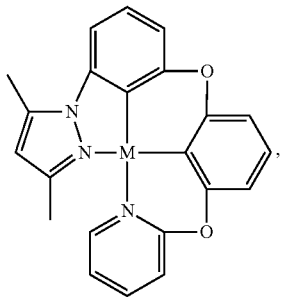

wherein M can comprise platinum (Pt-001), palladium, or combination thereof.

In another such aspect, the emitting component and the donor-acceptor component can form the following structure:

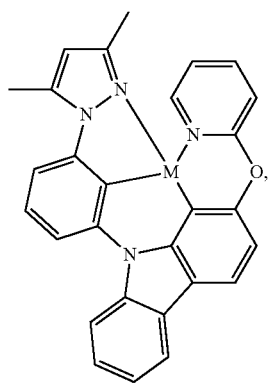

wherein M can comprise platinum (Pt-008), palladium, or combination thereof.

In yet another such aspect, the emitting component and the donor-acceptor component can form the following structure:

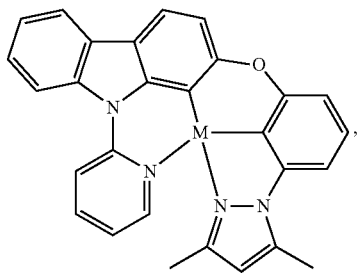

wherein M can comprise platinum (Pt-009), palladium, or combination thereof.

In one aspect, the use of a specific donor-acceptor component can create a unique distortion in the resulting complex. Each such distortion can provide an emission spectra having a unique shape or profile.

Thus, in one aspect, the specific emission spectra of a complex can be tuned by selecting appropriate donor-acceptor components. By then selecting one or more complexes having desired emission profiles, a lighting device can be created for an intended purpose. For example, a white OLED can be prepared using one or more inventive complexes of the present disclosure.

In various aspects, the inventive composition can be represented by one or more of the formulas illustrated herein. For any of the formulas illustrated in this disclosure, -A- can be represented by one or more of the following:

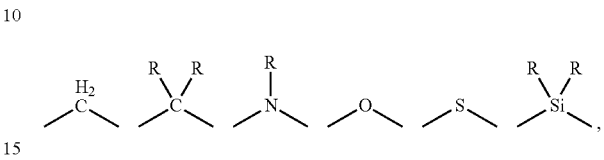

—U— can be represented by one or more of the following:

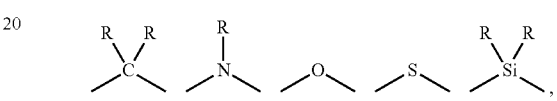

-Ph can be represented by one or more of the following:

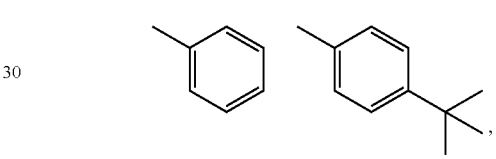

—V— can be represented by one or more of the following

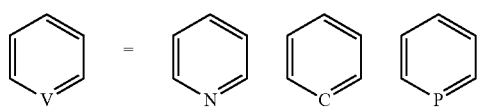

and -M- can be represented by Pt, Pd, or a combination thereof.

In another aspect, any recitation or illustration of:

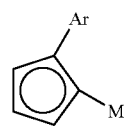

in a structure can include compositions wherein the group comprises one or more of the following:

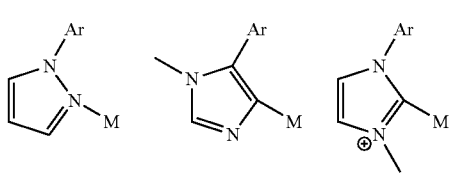

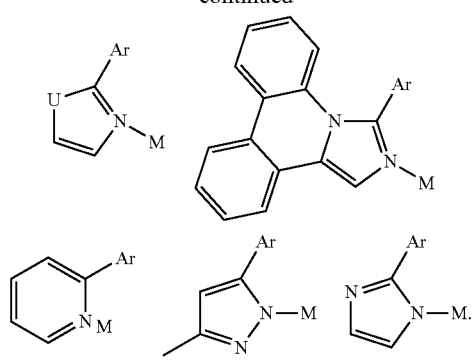
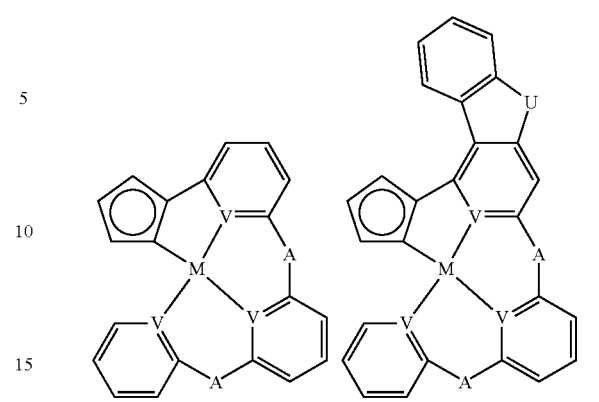

In yet another aspect, any recitation or illustration of:

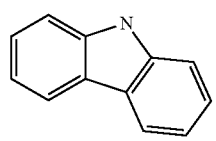 [SMILES: c1ccc2c(c1)[nH]c1ccccc12]

in a structure can include compositions wherein the group comprises one or more of the following:

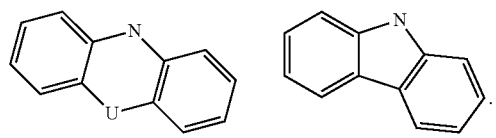

In yet another aspect, any recitation or illustration of:

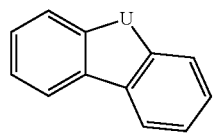

in a structure can include compositions wherein the group comprises one or more of the following:

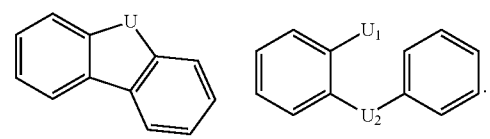

In various aspects, specific non-limiting examples of the inventive composition can be represented by one or more of the following formulas:

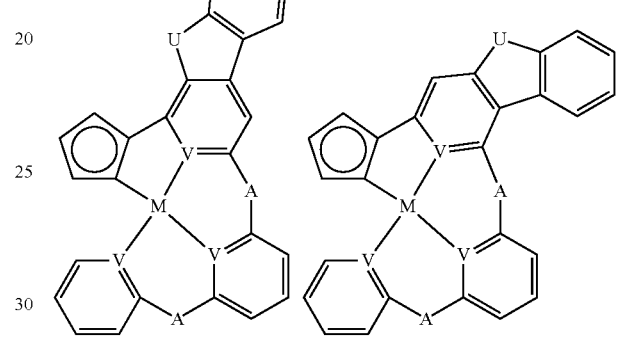
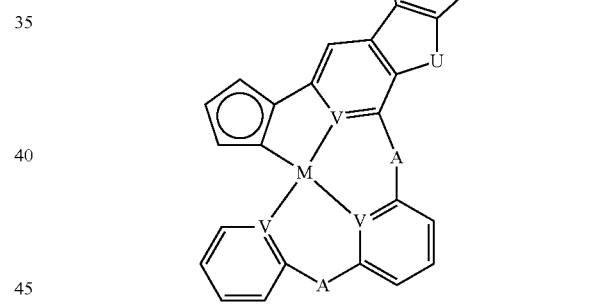
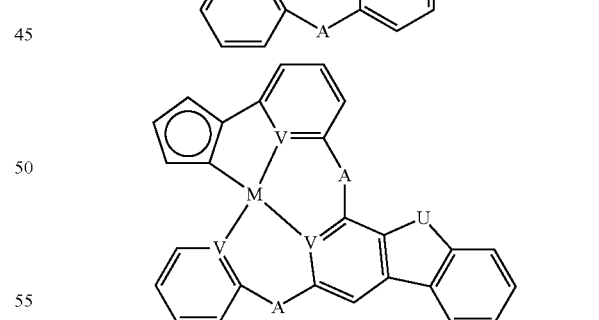
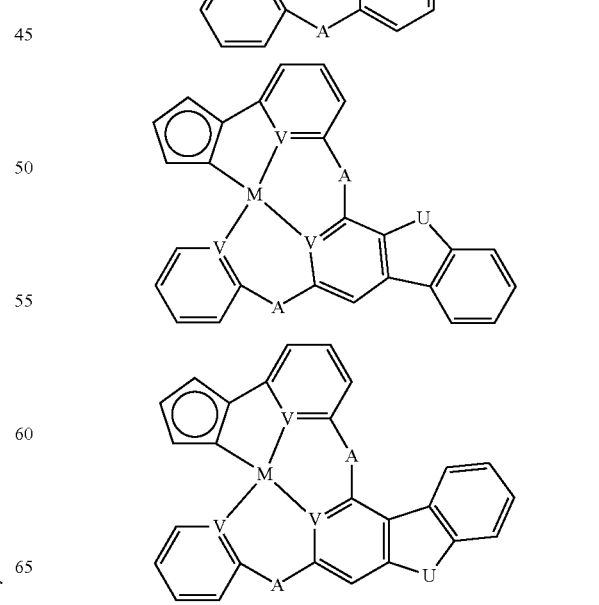

-continued
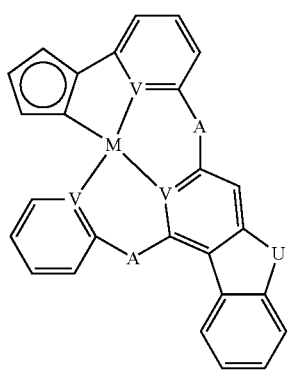
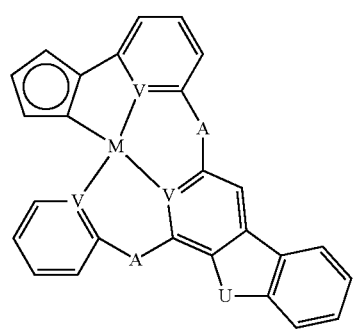
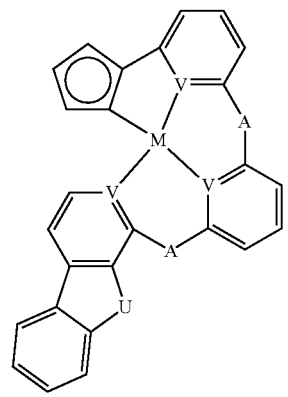
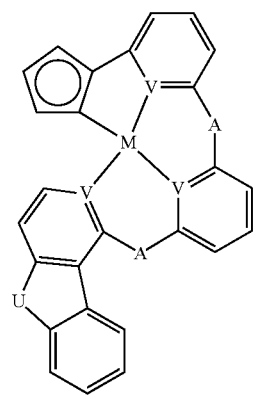
-continued
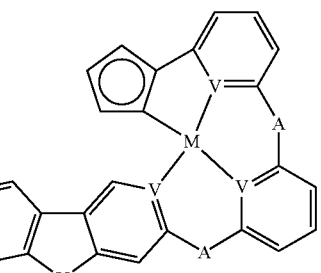
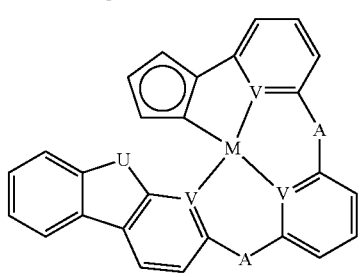
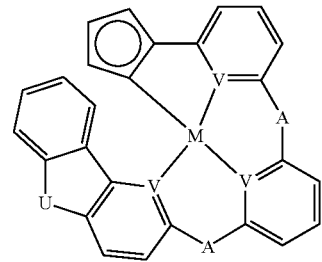
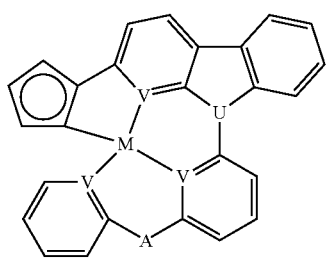
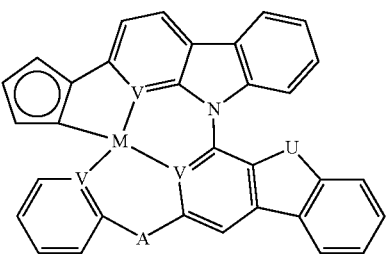

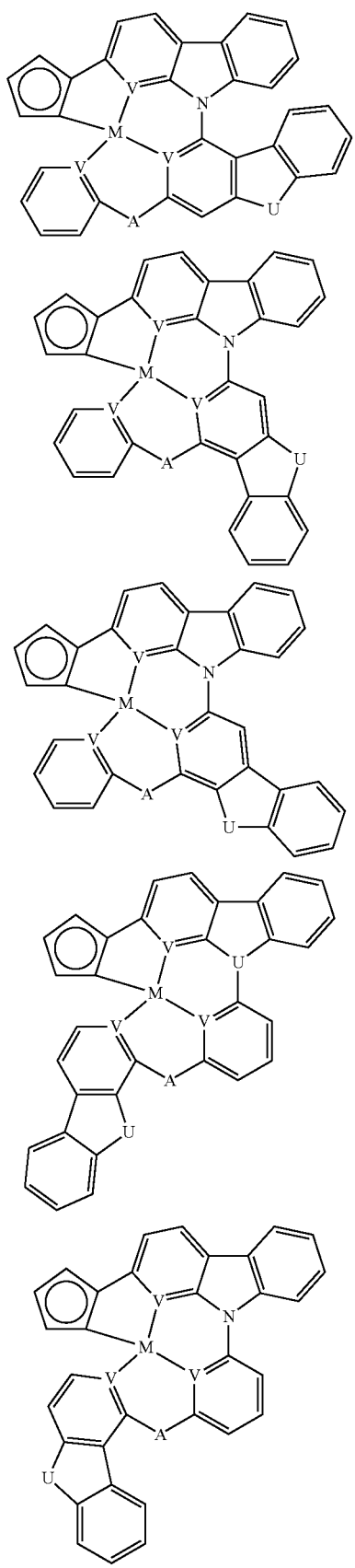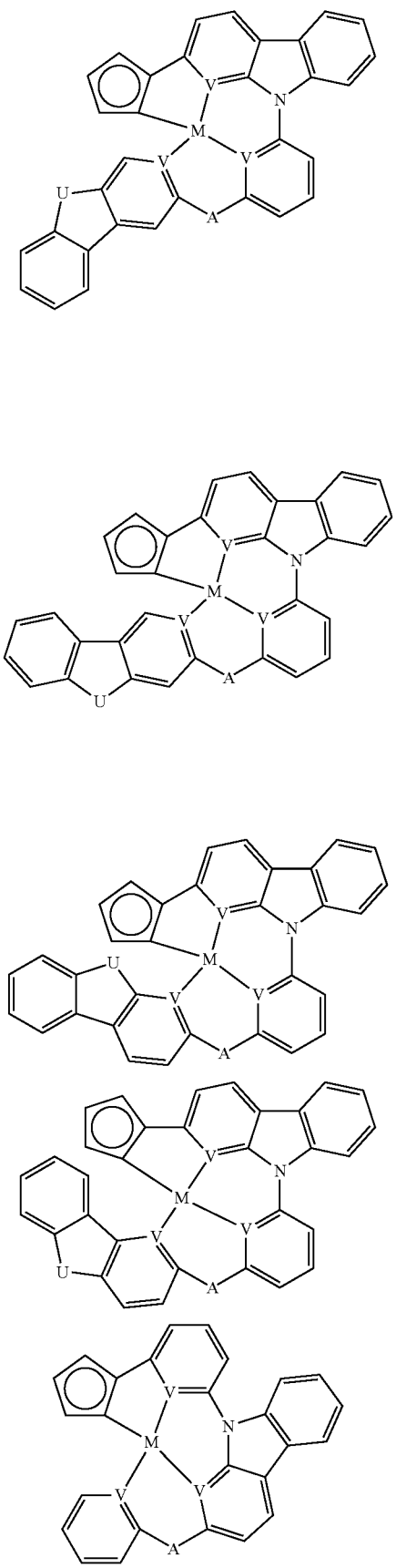

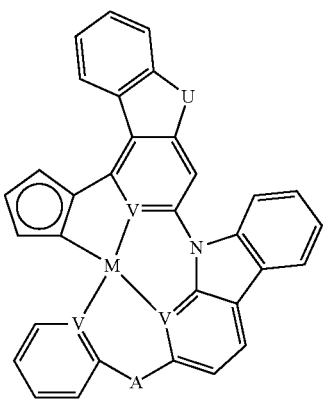
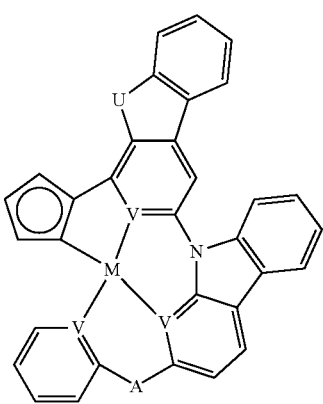
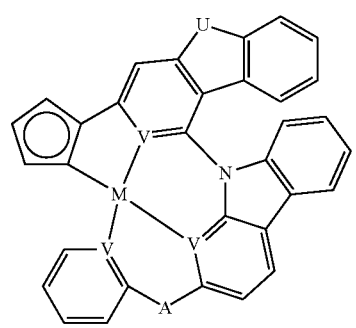
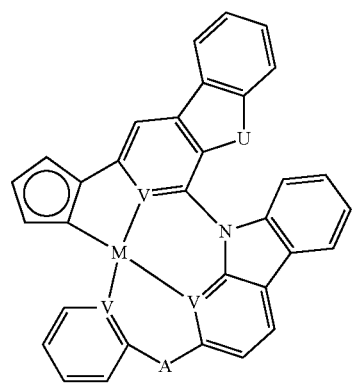
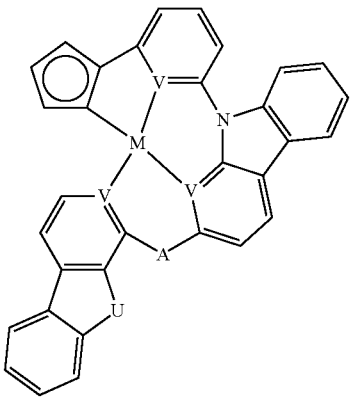
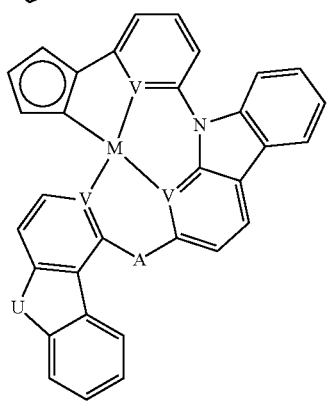
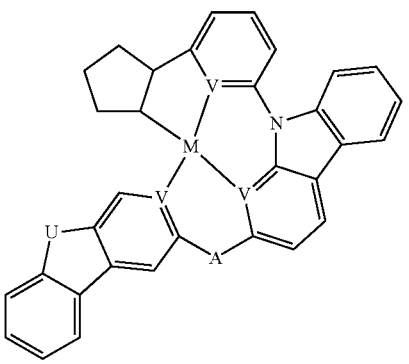
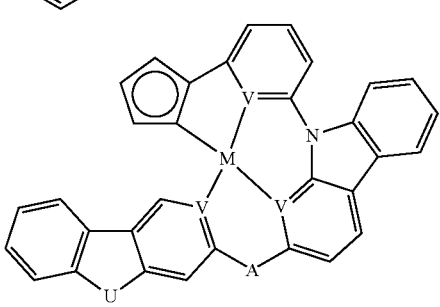
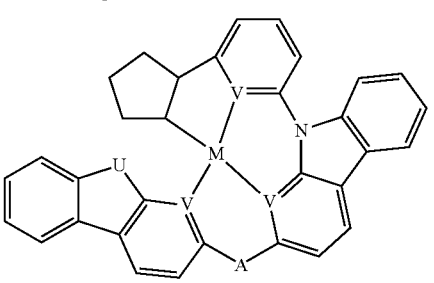

-continued
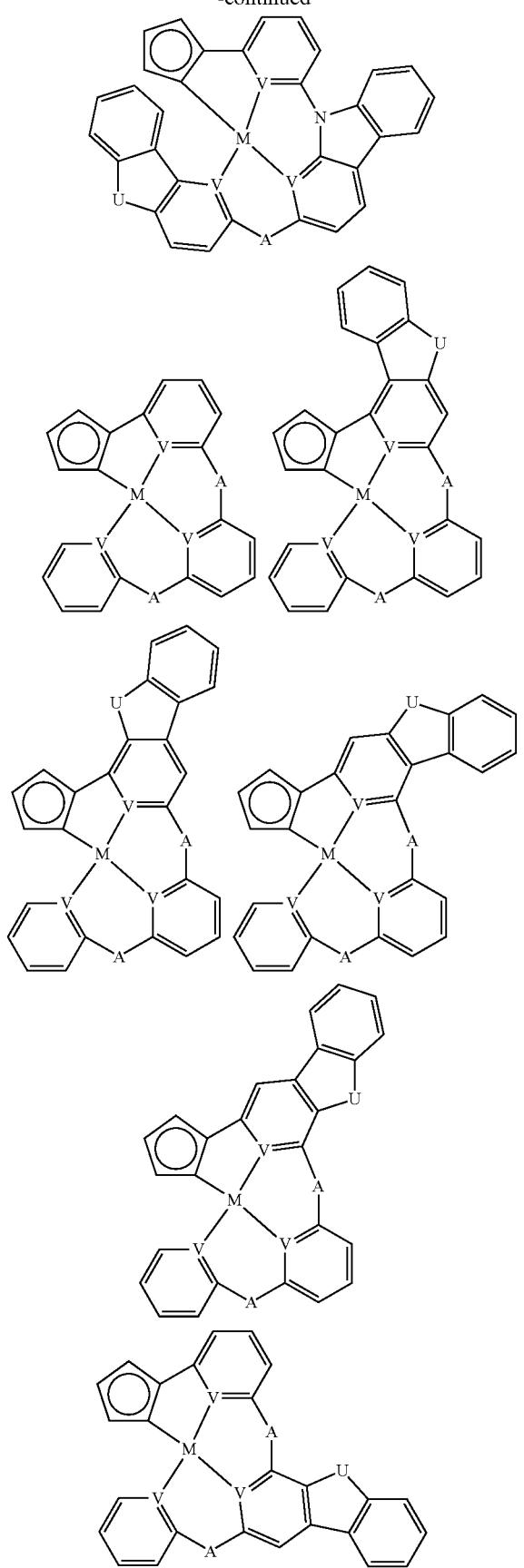
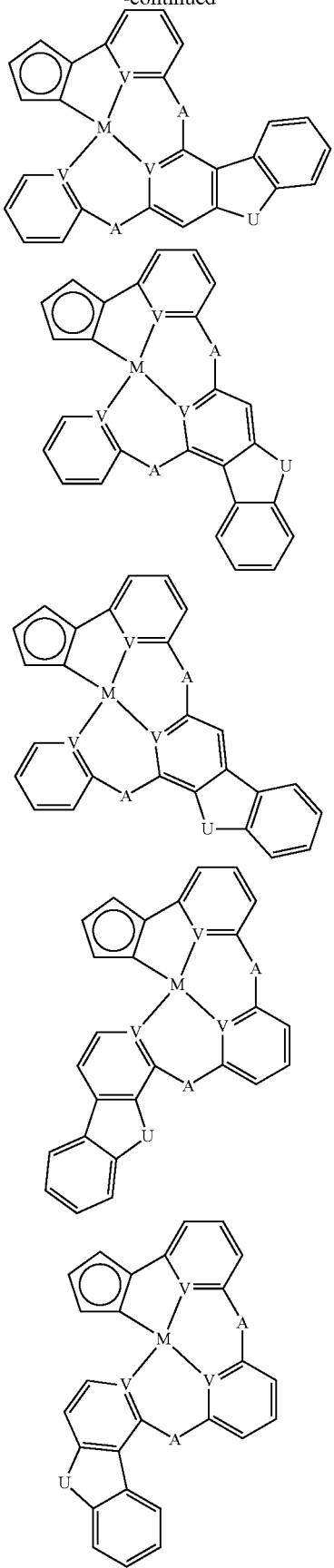

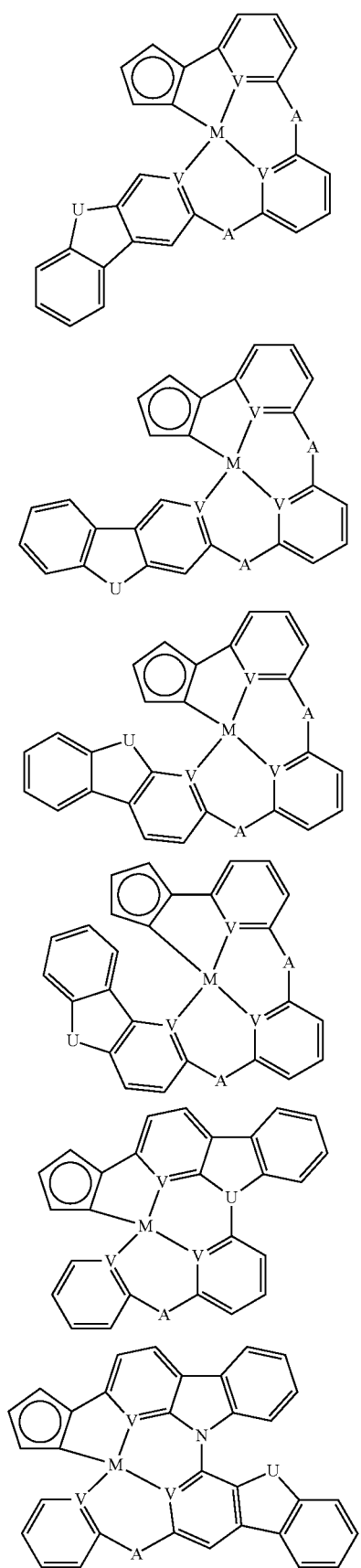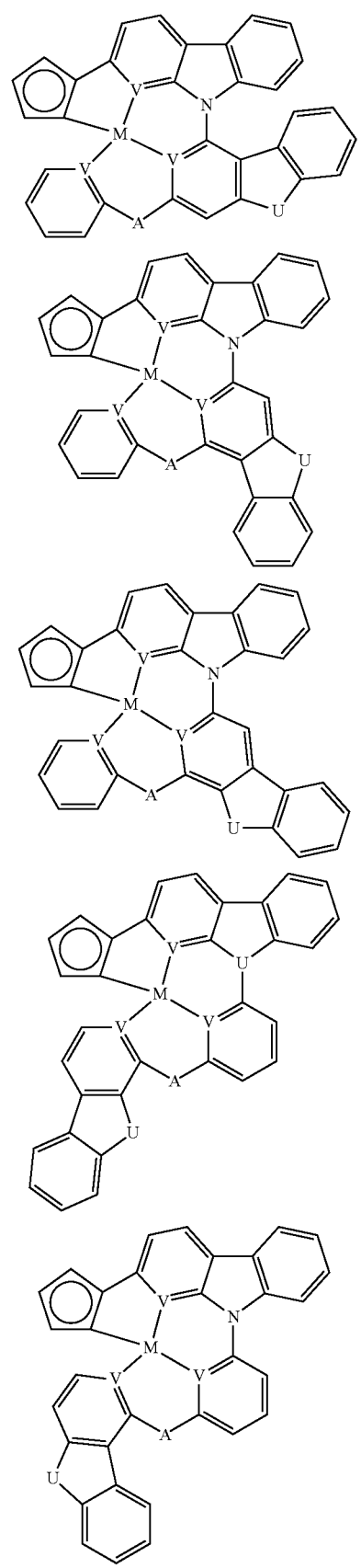

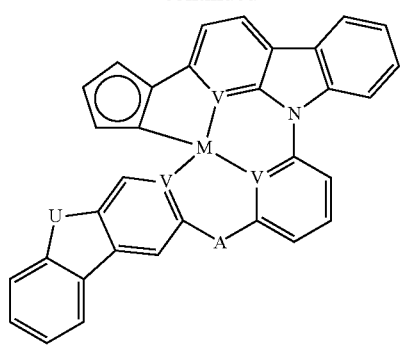
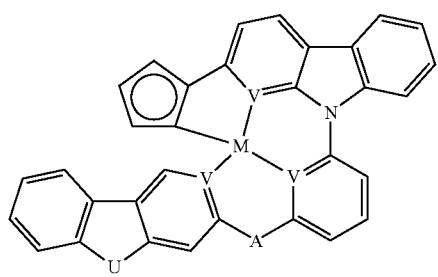
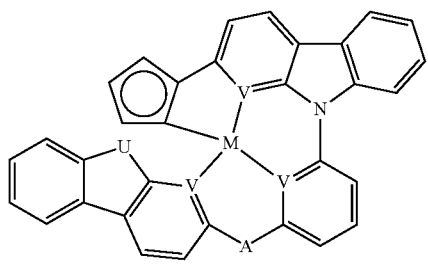
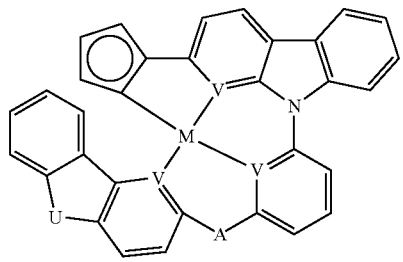
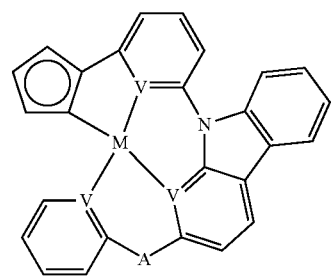
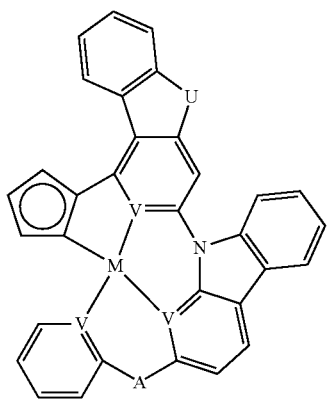
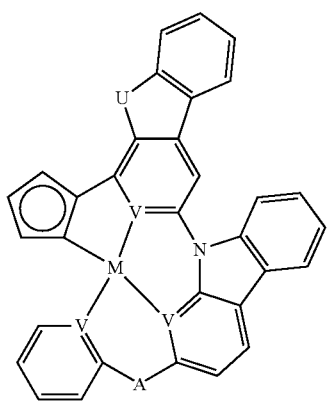
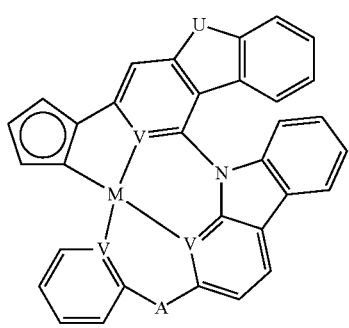
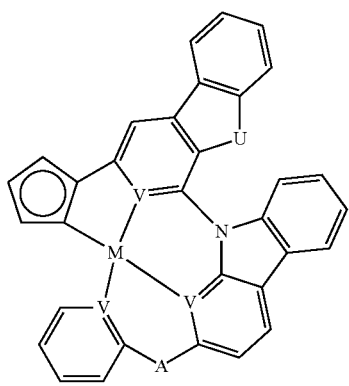

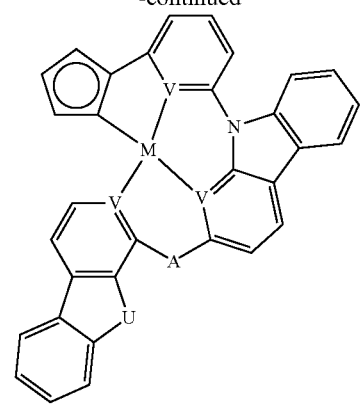
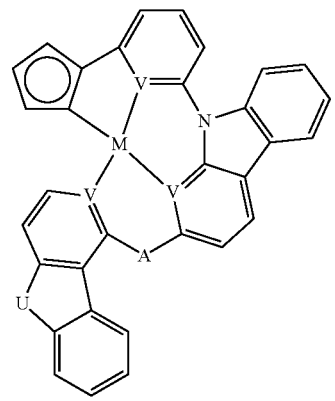
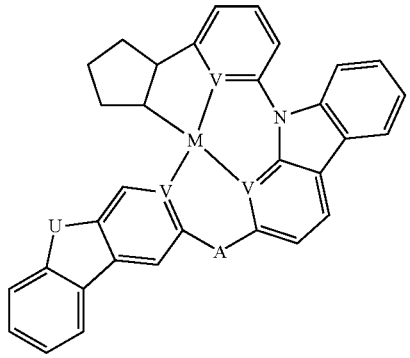
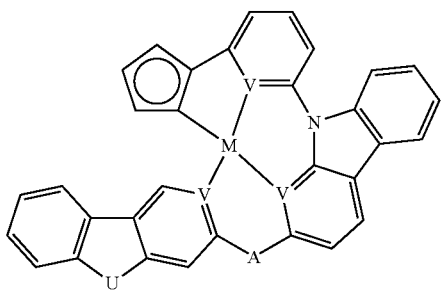
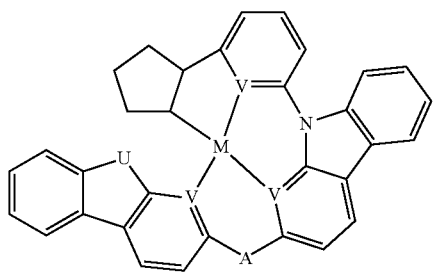
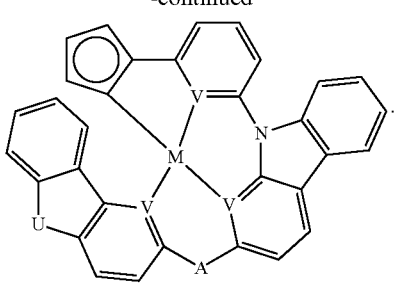
In another aspect, the inventive complex the inventive complex can be represented by one or more of the following:
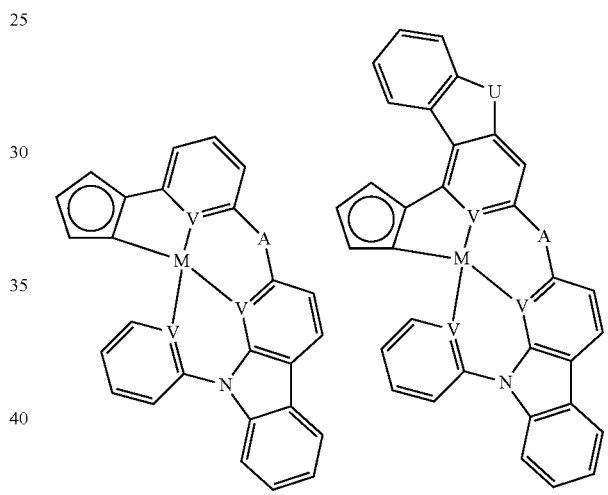
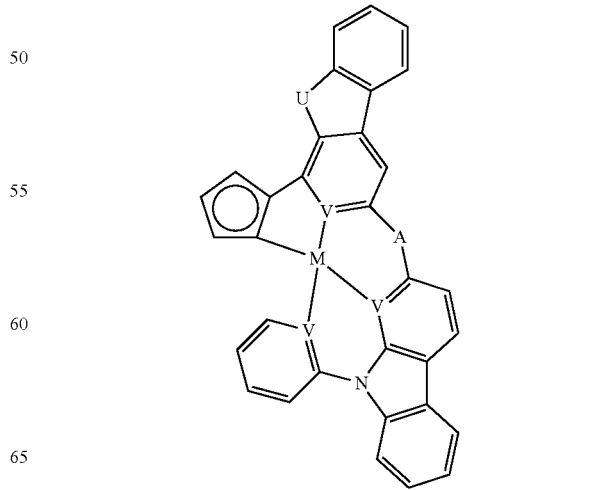

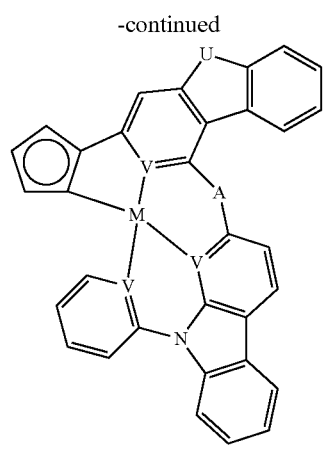
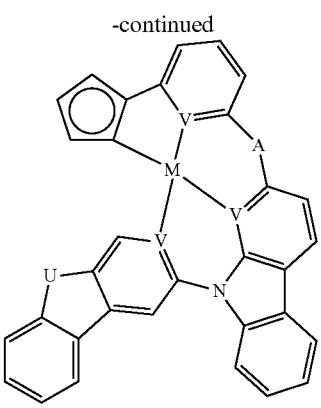
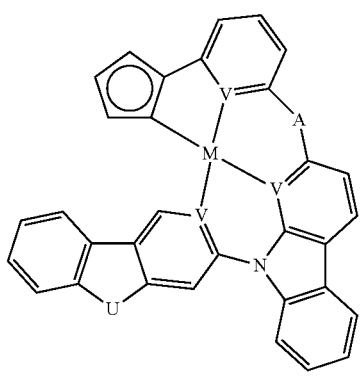
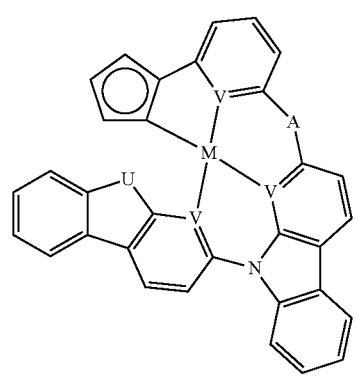
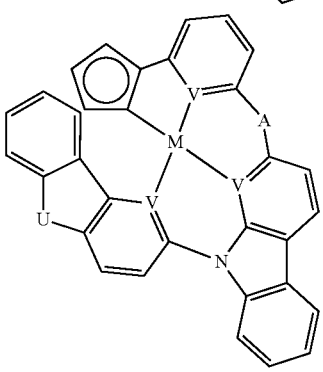

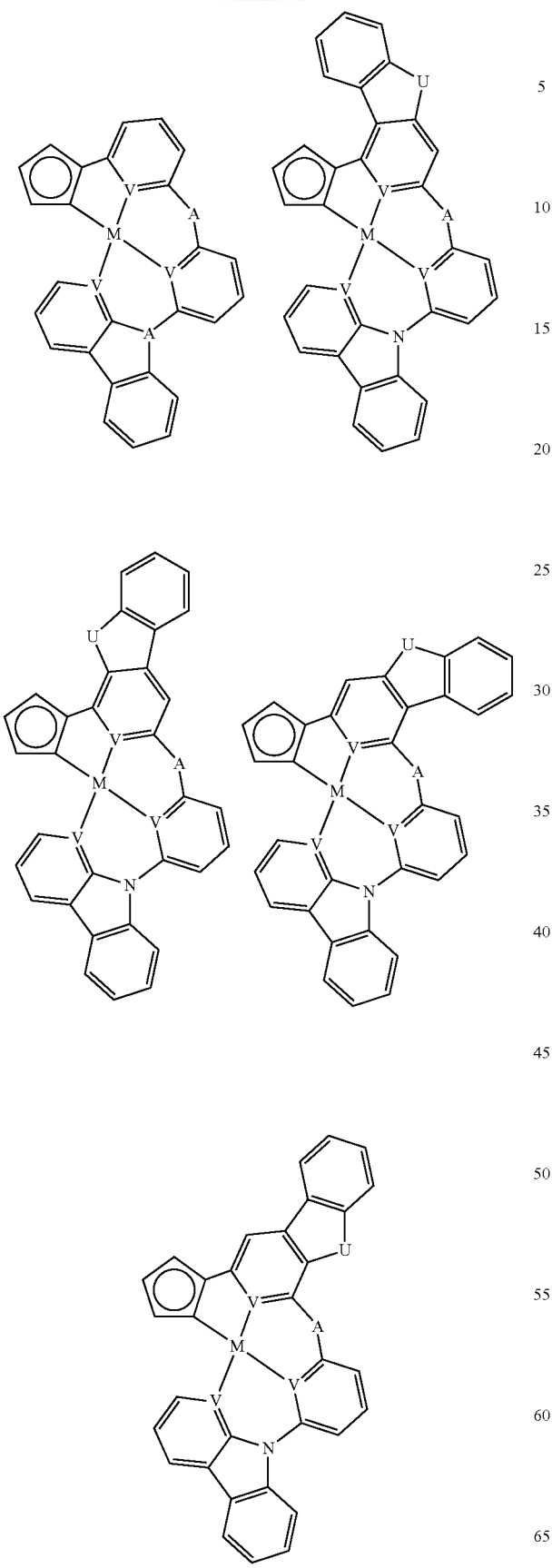
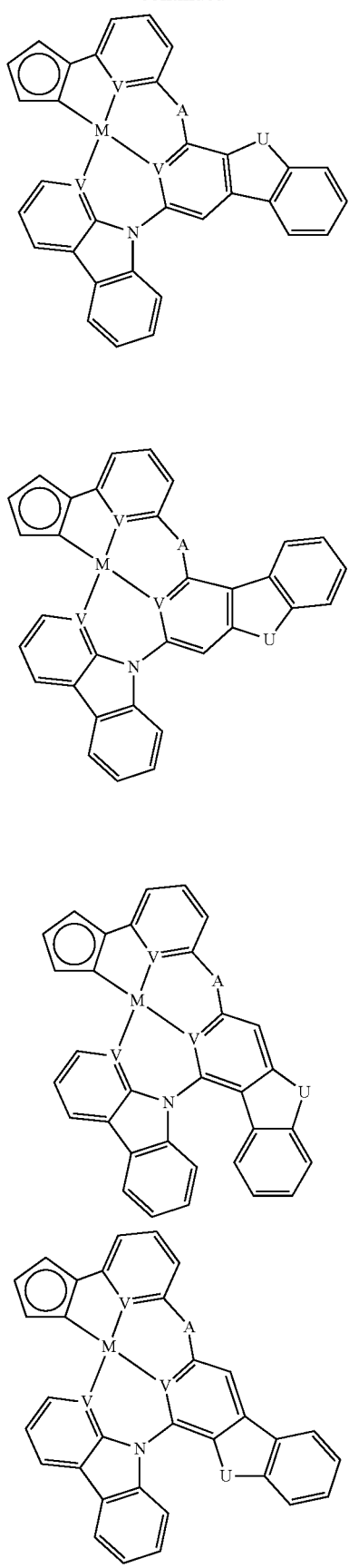

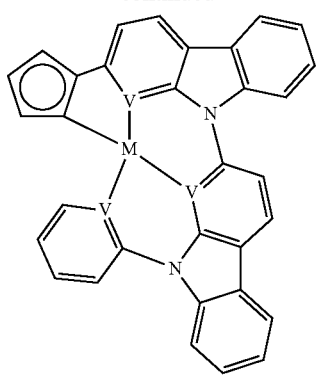
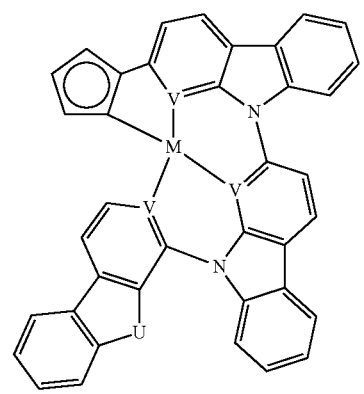
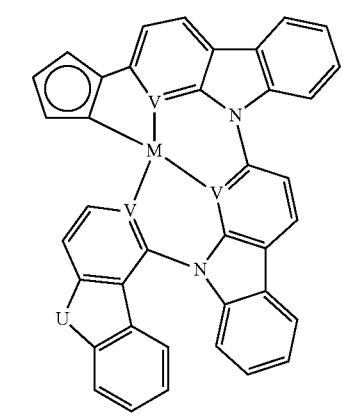
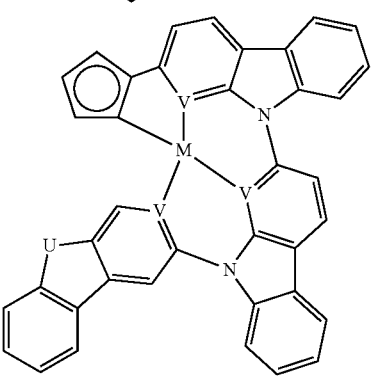
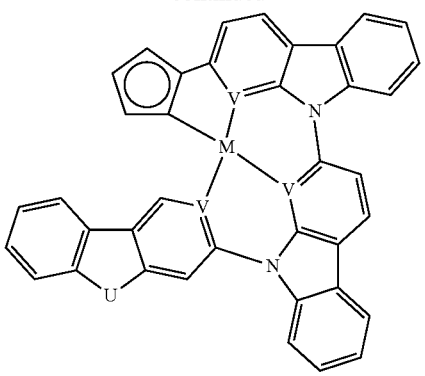
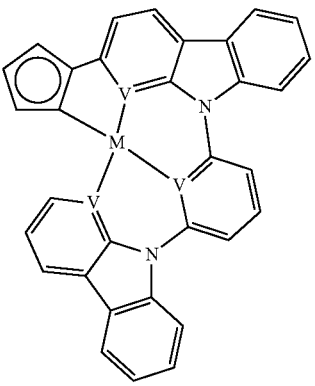
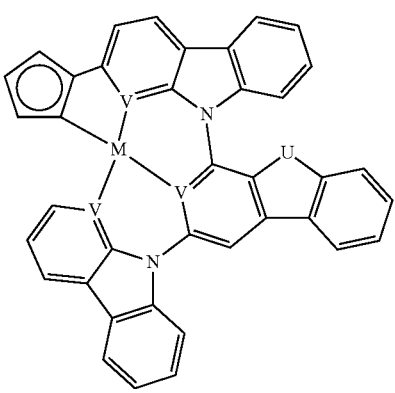
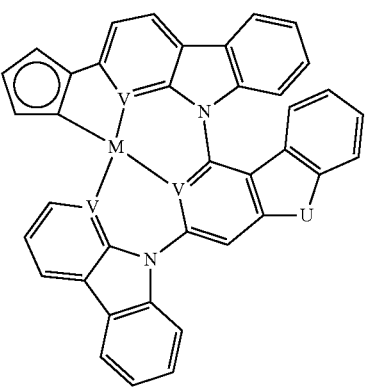

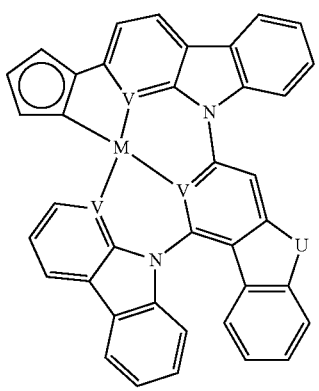
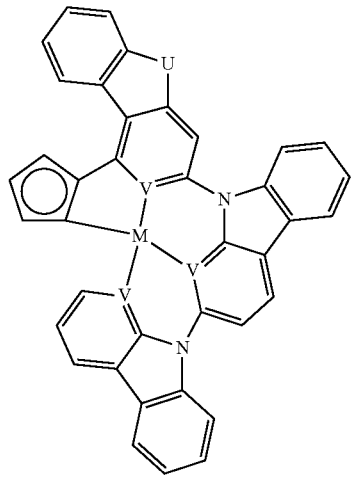
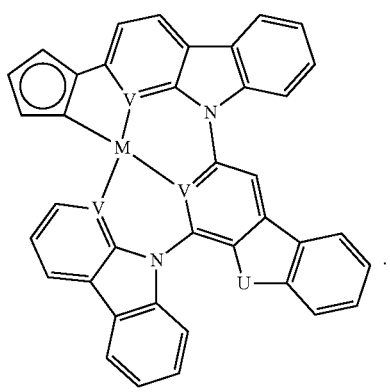
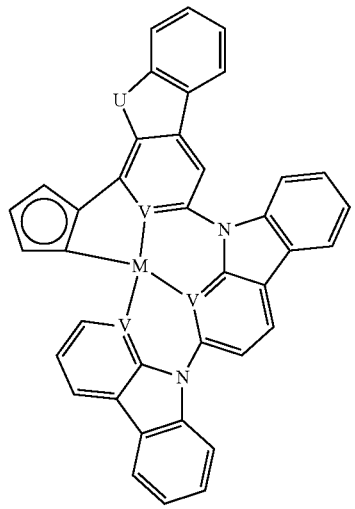
In yet another aspect, the inventive complex can be represented by one or more of the following:
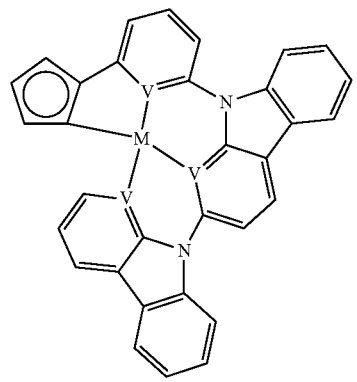
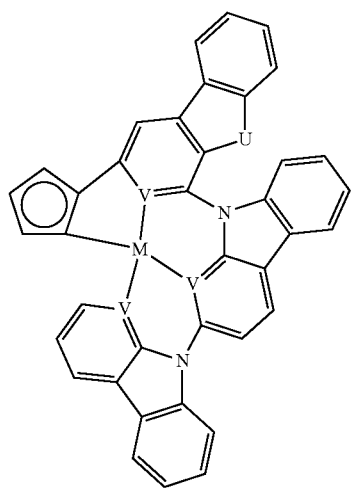

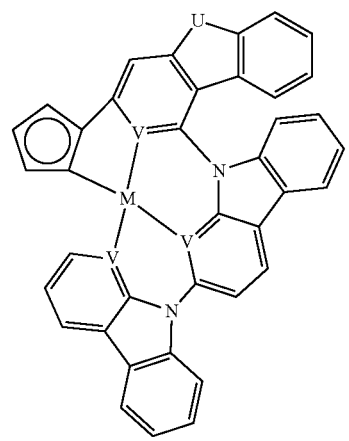
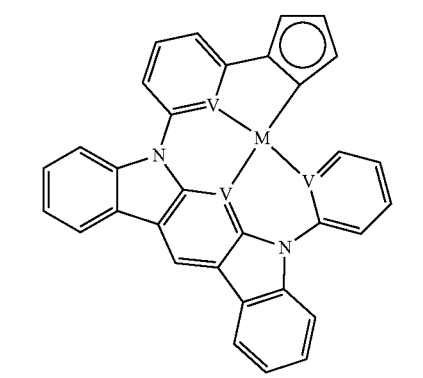
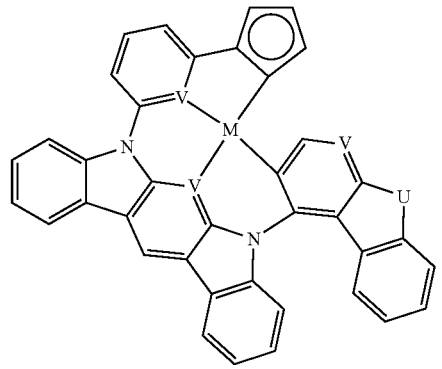
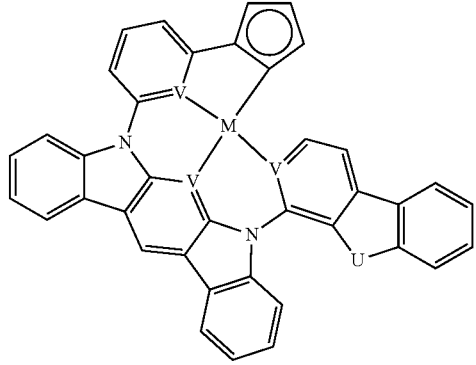
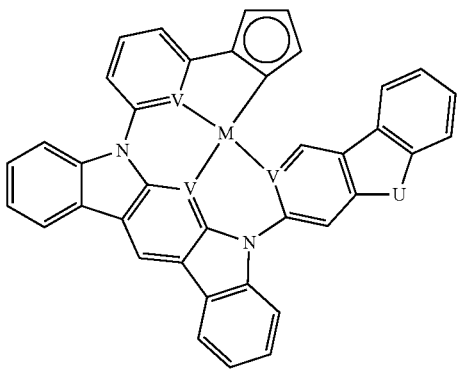
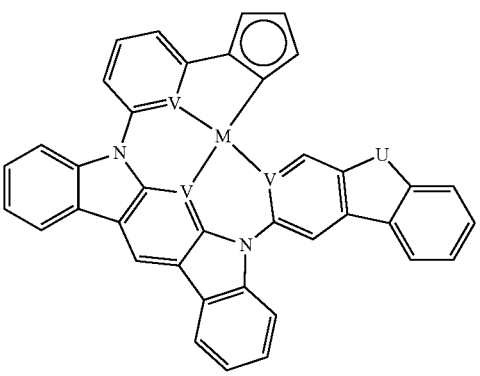
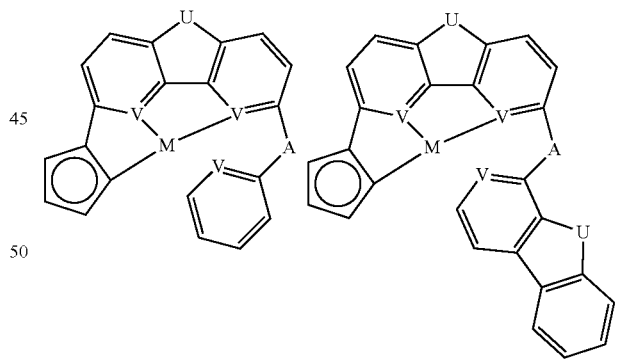
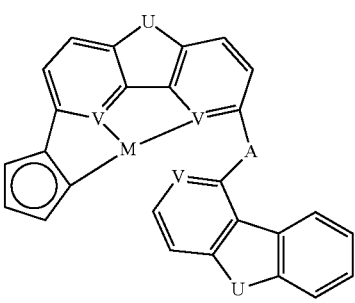

-continued
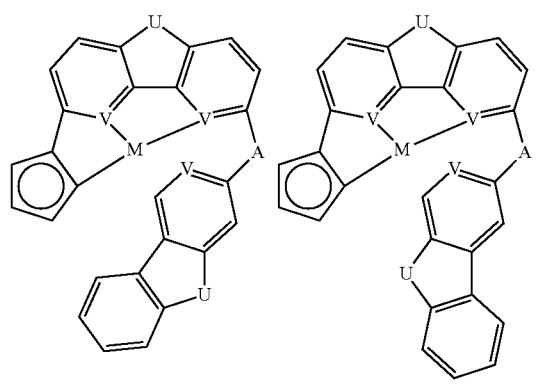
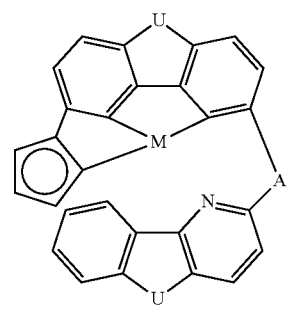
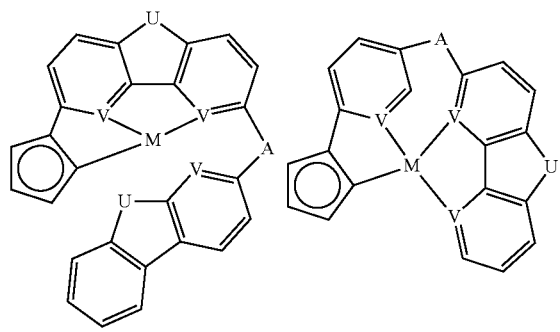
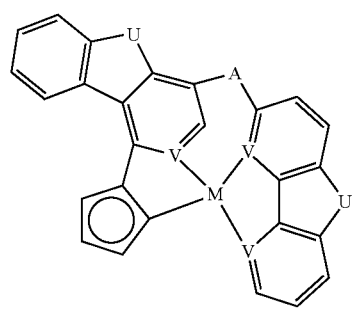
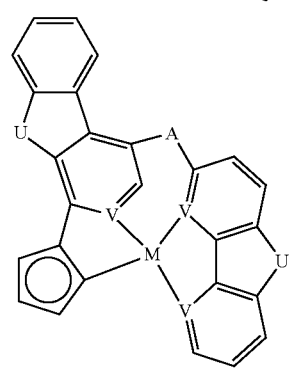
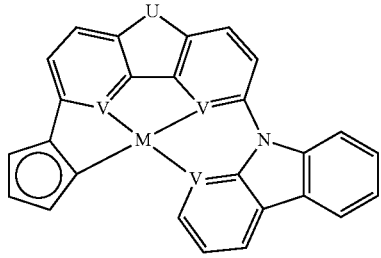
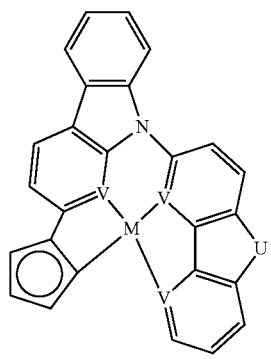
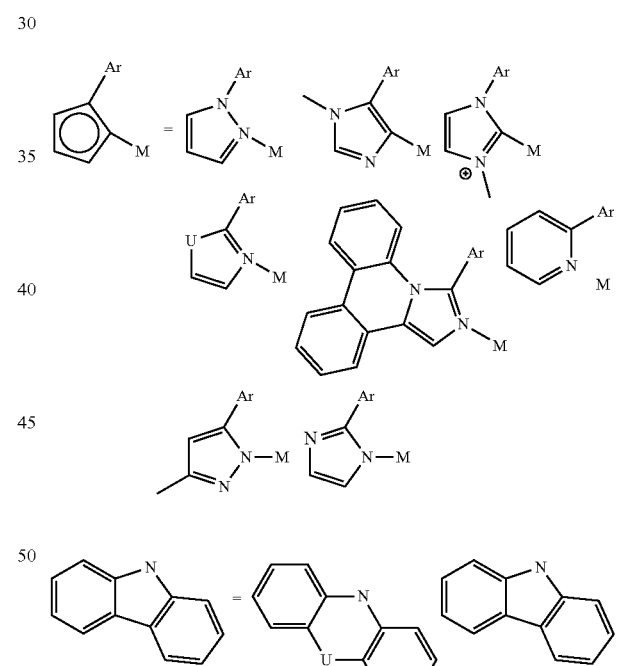
In another aspect, the inventive complex is a platinum complex comprising one or more of the following formulas:

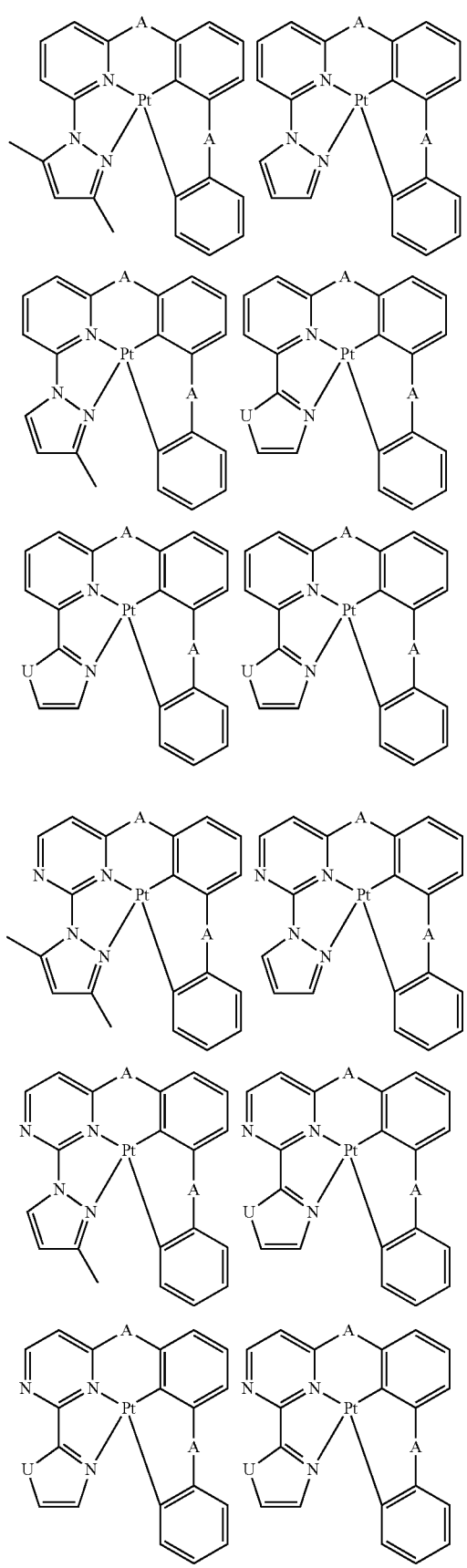
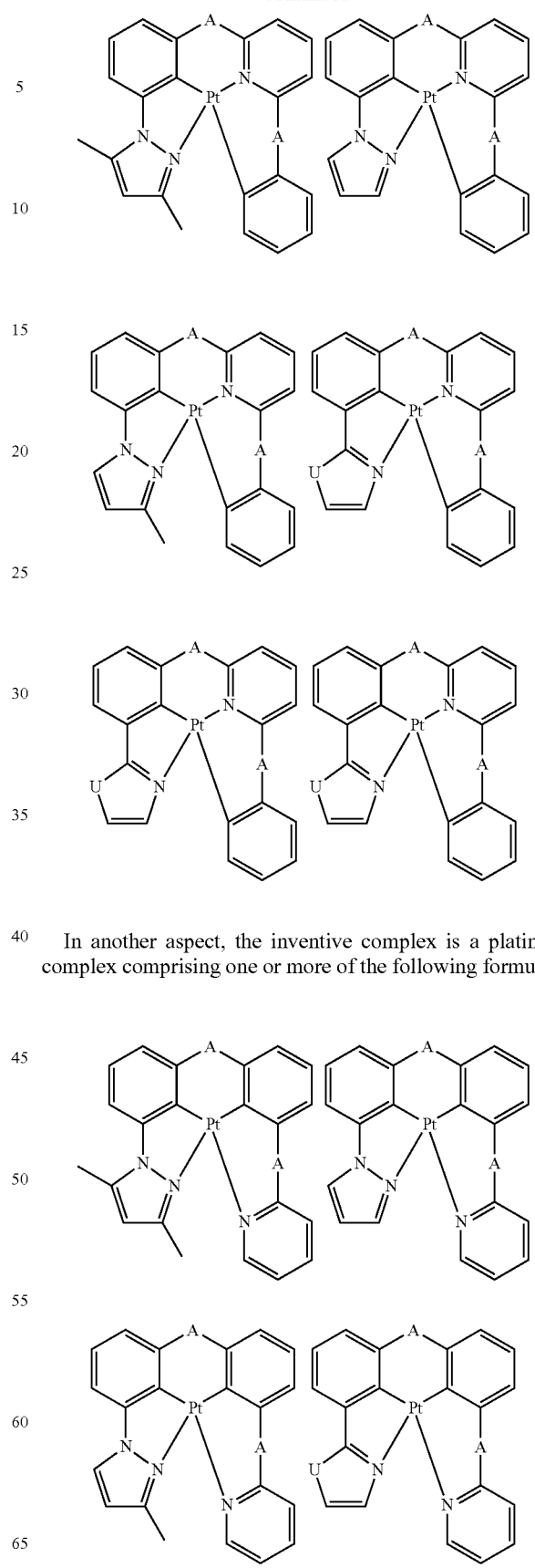
In another aspect, the inventive complex is a platinum complex comprising one or more of the following formulas:

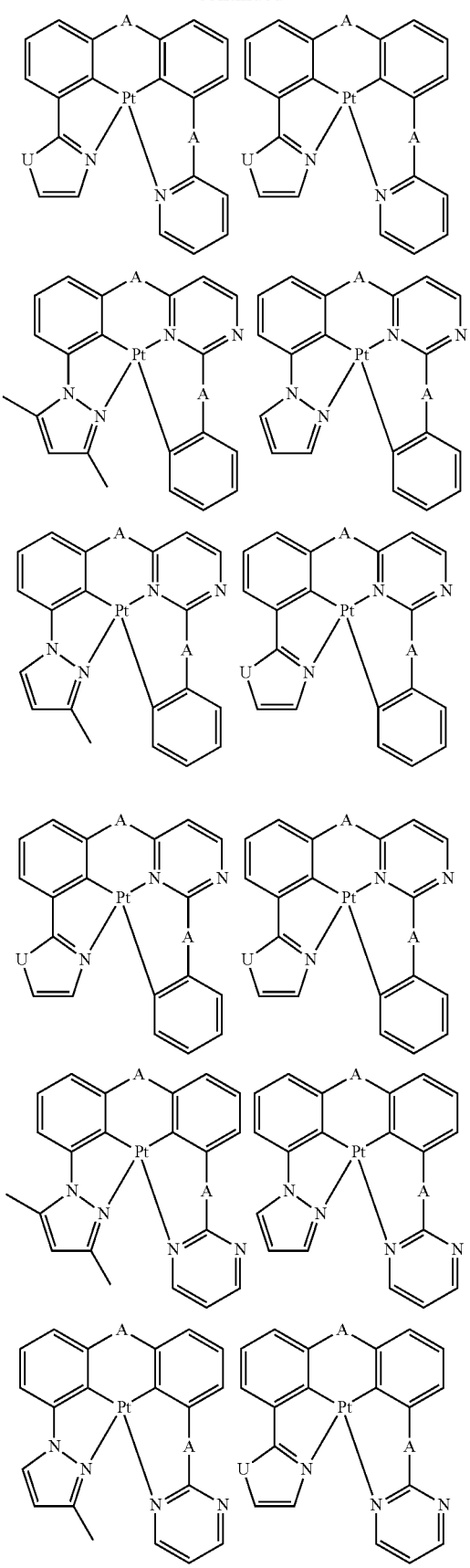
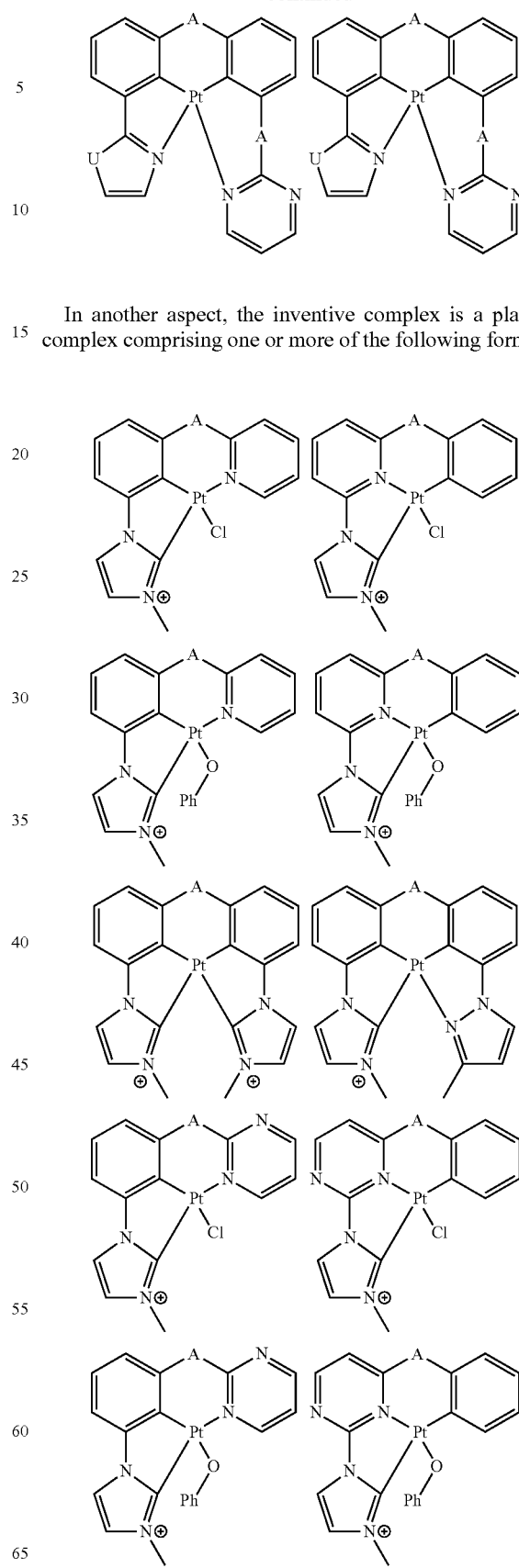
In another aspect, the inventive complex is a platinum complex comprising one or more of the following formulas:

-continued

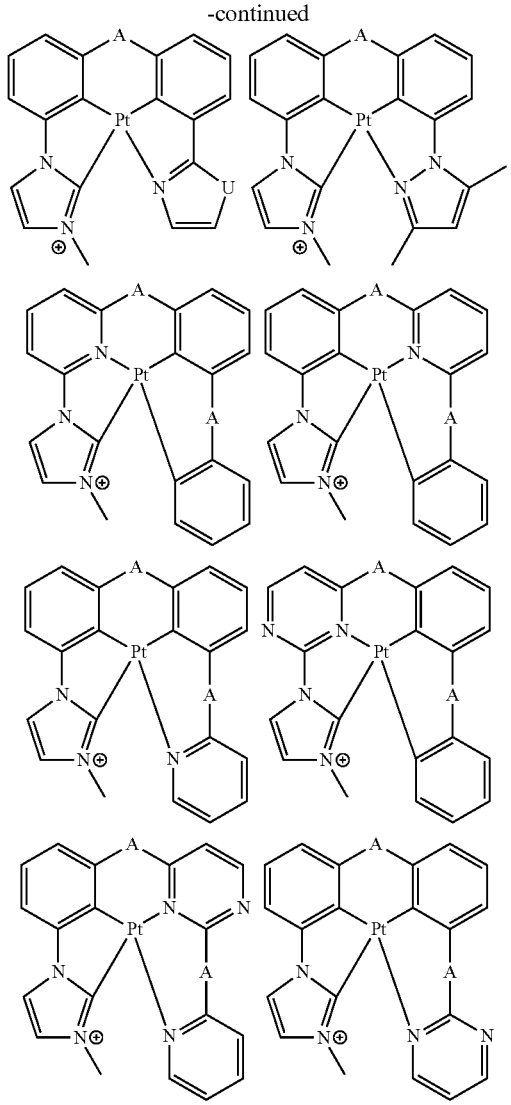

In another aspect, the inventive complex is a platinum complex comprising one or more of the following formulas:

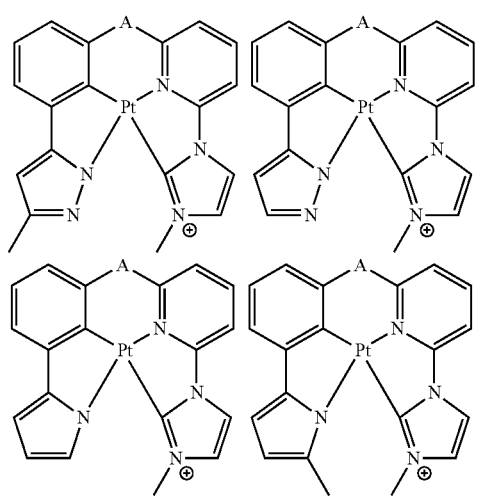

-continued

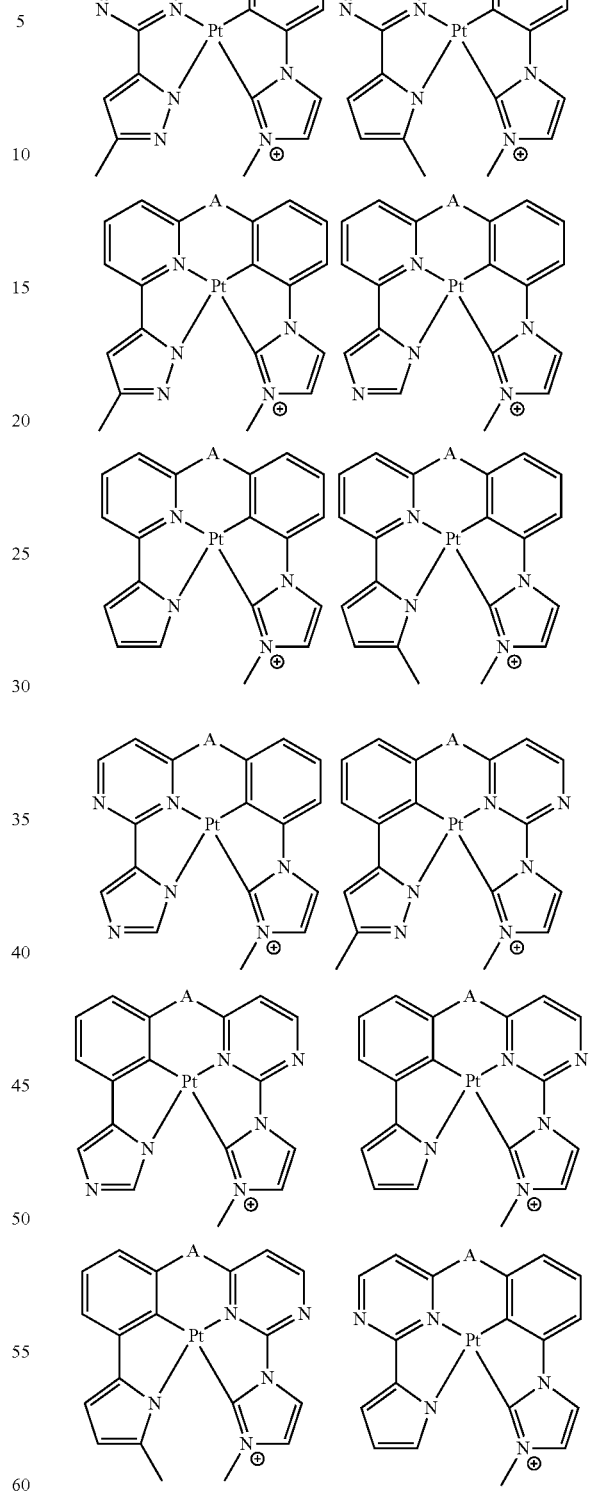

In another aspect, the above compounds comprise a palladium atom as a metal center.

In another aspect, the inventive complex is not any one or more of the compounds described or illustrated herein. In an exemplary aspect, the inventive complex is not:

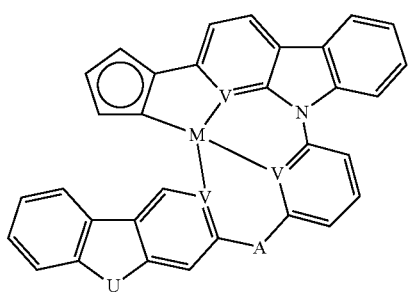

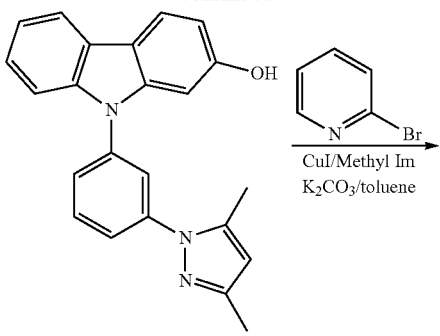

N-(3,5-Dimethylpyrazolylphenyl)-2-hydroxycarbazole

The above exemplary aspect is not intended to be limiting, but instead representative of aspects wherein any one or a combination of compounds described or illustrated herein are excluded from the invention.

The inventive complexes can be prepared using conventional chemical synthesis techniques. Several synthetic schemes are illustrated herein, but the invention is not intended to be limited to the recited schemes. Temperatures, catalysts, concentrations, reactant compositions, and other process conditions can vary, and one of skill in the art, in possession of this disclosure, could readily select appropriate reactants and conditions for a desired complex.

In one aspect, a complex, such as, for example, a Pt-001 complex, can be prepared by first preparing a 3-(pyridine-2-yloxy)phenol. This species can then be reacted to form 2-(3-(3-bromophenoxy)phenoxy)pyridine, which can be further reacted to form 2-(3-(3-(3,5-dimethyl-1H-pyrazol-1-yl)phenoxy)phenoxy)pyridine. This species can then be reacted to form the Pt-001 complex.

In another aspect, a Pt-008 complex can be prepared according to the following scheme.

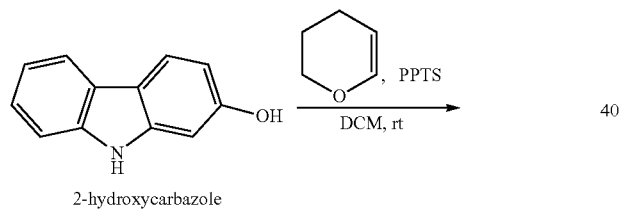

2-hydroxycarbazole

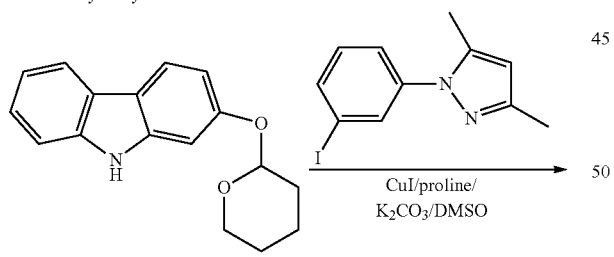

2-tetrahydropyranyloxycarbazole

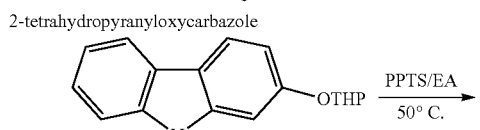

N-[3-(3,5-Dimethylpyrazolylphenyl)]-2-tetrahydropyranyloxycarbazole

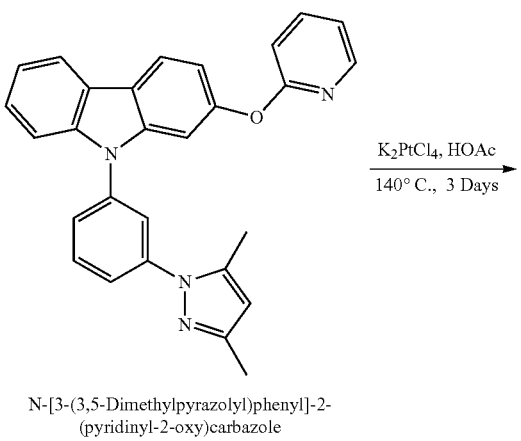

N-[3-(3,5-Dimethylpyrazolyl)phenyl]-2-(pyridinyl-2-oxy)carbazole

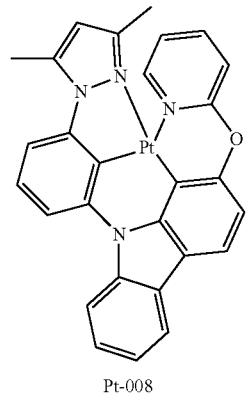

Pt-008

In yet another aspect, a Pt-009 complex can be prepared according to the following scheme:

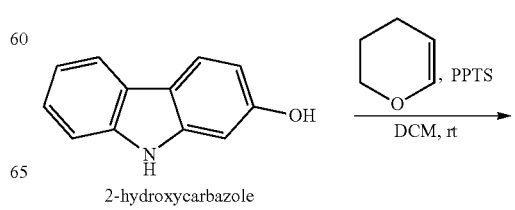

2-hydroxycarbazole

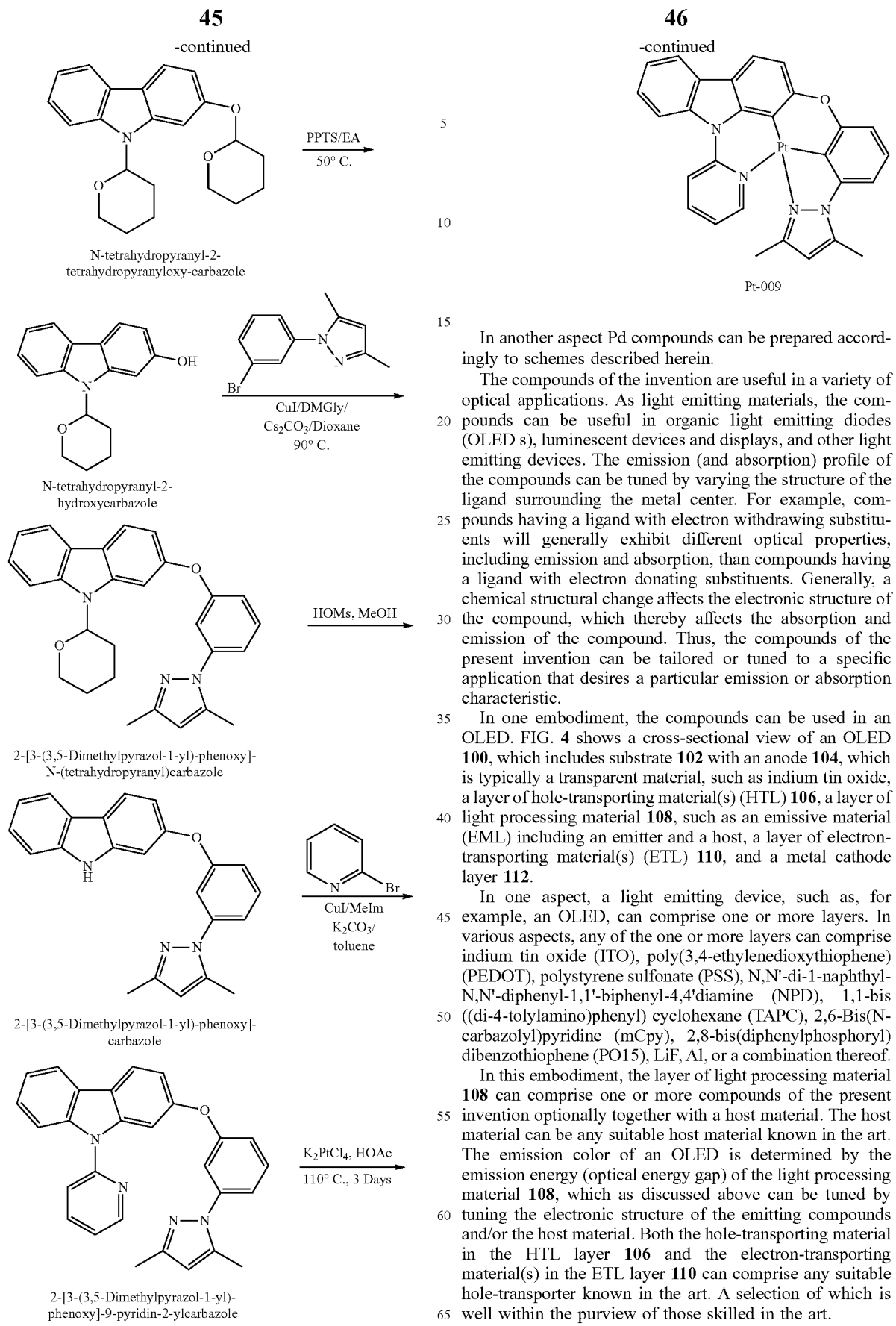

In another aspect Pd compounds can be prepared accordingly to schemes described herein.

The compounds of the invention are useful in a variety of optical applications. As light emitting materials, the compounds can be useful in organic light emitting diodes (OLED s), luminescent devices and displays, and other light emitting devices. The emission (and absorption) profile of the compounds can be tuned by varying the structure of the ligand surrounding the metal center. For example, compounds having a ligand with electron withdrawing substituents will generally exhibit different optical properties, including emission and absorption, than compounds having a ligand with electron donating substituents. Generally, a chemical structural change affects the electronic structure of the compound, which thereby affects the absorption and emission of the compound. Thus, the compounds of the present invention can be tailored or tuned to a specific application that desires a particular emission or absorption characteristic.

Figure 4:
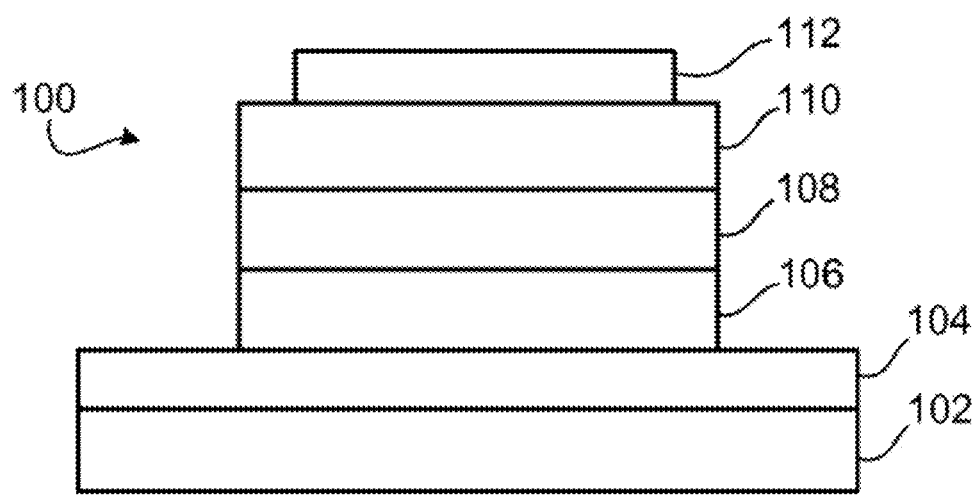
FIG. 4 is a drawing of a cross-section of an exemplary organic light-emitting diode (OLED).

In one embodiment, the compounds can be used in an OLED. FIG. 4 shows a cross-sectional view of an OLED 100, which includes substrate 102 with an anode 104, which is typically a transparent material, such as indium tin oxide, a layer of hole-transporting material(s) (HTL) 106, a layer of light processing material 108, such as an emissive material (EML) including an emitter and a host, a layer of electron-transporting material(s) (ETL) 110, and a metal cathode layer 112.

In one aspect, a light emitting device, such as, for example, an OLED, can comprise one or more layers. In various aspects, any of the one or more layers can comprise indium tin oxide (ITO), poly(3,4-ethylenedioxythiophene) (PEDOT), polystyrene sulfonate (PSS), N,N'-di-1-naphthyl-N,N'-diphenyl-1,1'-biphenyl-4,4'diamine (NPD), 1,1-bis((di-4-tolylamino)phenyl) cyclohexane (TAPC), 2,6-Bis(N-carbazolyl)pyridine (mCpy), 2,8-bis(diphenylphosphoryl) dibenzothiophene (PO15), LiF, Al, or a combination thereof.

In this embodiment, the layer of light processing material 108 can comprise one or more compounds of the present invention optionally together with a host material. The host material can be any suitable host material known in the art. The emission color of an OLED is determined by the emission energy (optical energy gap) of the light processing material 108, which as discussed above can be tuned by tuning the electronic structure of the emitting compounds and/or the host material. Both the hole-transporting material in the HTL layer 106 and the electron-transporting material(s) in the ETL layer 110 can comprise any suitable hole-transporter known in the art. A selection of which is well within the purview of those skilled in the art.

It will be apparent that the compounds of the present invention can exhibit phosphorescence. Phosphorescent OLEDs (i.e., OLEDs with phosphorescent emitters) typically have higher device efficiencies than other OLEDs, such as fluorescent OLEDs. Light emitting devices based on electrophosphorescent emitters are described in more detail in WO2000/070655 to Baldo et al., which is incorporated herein by this reference for its teaching of OLEDs, and in particular phosphorescent OLEDs.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric. Unless indicated otherwise, in all examples described herein, Pt and/or Pd atoms can be used in each other's place, such that both aspects comprising Pt and aspects comprising Pd are disclosed.

Example 1: Pt-001

In a first example, a Pt-001 complex, as described herein, was synthesized. Initially, 3-(pyridine-2-yloxy)phenol was synthesized. Under a nitrogen atmosphere, a pressure vessel was charged with a magnetic stir bar, resorcinol (110 mmol), 2-bromopyridine (100 mmol), 1-methylimidazole (5 mmol), and potassium carbonate (200 mmol). Pyridine (80 mL) was added and bubbled with nitrogen for 20 minutes before copper(I) iodide (10 mmol) was added and bubbled 10 minutes further. The vessel was sealed and heated to 140° C. while stirring. After 2 days, the solution was allowed to cool. The solids were then filtered off and rinsed with a 50:50 mixture of toluene and methanol. The filtrate was reduced by rotary evaporation and 150 ml of water containing 10 mL glacial acetic acid was added and shaken vigorously. The water was decanted off and 50 mL of DCM was added, forming an off white precipitate which was collected by vacuum filtration and dried with ether, resulting in the pure product 3-(pyridin-2-yloxy)phenol with a 55% yield.

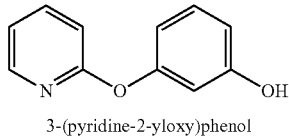 [SMILES: Oc1cccc(Oc2ccccn2)c1]

3-(pyridine-2-yloxy)phenol

In another step, 2-(3-(3-bromophenoxy)phenoxy)pyridine was synthesized. Under a nitrogen atmosphere, a pressure vessel was charged with a magnetic stir bar, 3-(pyridin-2-yloxy)phenol (50 mmol) as produced above, 2,6-dibromopyridine (50 mmol), 1-methylimidazole (25 mmol), and potassium carbonate (100 mmol). Toluene (80 mL) was added and bubbled with nitrogen for 20 minutes before copper(I) iodide (5 mmol) was added and the solution bubbled for 10 minutes further. The vessel was sealed and heated to 140° C. while stirring. After 2 days, the solution was allowed to cool and the solids were filtered off and rinsed with dichloromethane. The filtrate was added to a separatory funnel containing DCM and water. The water phase was washed 3 times with 75 mL DCM, and the combined organic layers were washed once with pure water. The organic layer was then collected, dried with magnesium sulfate, filtered, and the filtrate reduced by rotary evaporation. The resulting oil was purified by column chromatography using DCM over silica resulting in the pure product 2-(3-(3-bromophenoxy)phenoxy)pyridine with a 60% yield. $^1$H NMR (CDCl$_3$): 6.80-6.85 (m, 2H), 6.91 (s, 1H), 6.94 (s, 1H), 6.97-7.03 (m, 2H), 7.19 (vt, 1H), 7.21-7.24 (m, 2H), 7.36 (vt, 1H), 7.70 (dd, 1H), 8.21 (dd, 1H).

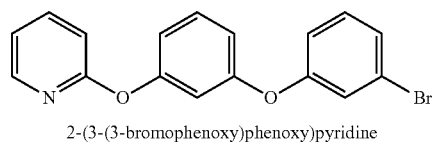 [SMILES: Brc1cccc(Oc2cccc(Oc3ccccn3)c2)c1]

2-(3-(3-bromophenoxy)phenoxy)pyridine

In another step, 2-(3-(3-(3,5-dimethyl-1H-pyrazol-1-yl)phenoxy)phenoxy)pyridine was synthesized. After standard cycles of evacuation and back-fill with dry and pure nitrogen, an oven-dried Schlenk flask equipped with a magnetic stir bar was charged with Cu$_2$O (1 mmol, 10 mol %), syn-2-pyridinealdoxime (4 mmol, 20 mol %), 3,5-dimethylpyrazole (12 mmol), Cs$_2$CO$_3$ (25 mmol), 2-(3-(3-(3,5-dimethyl-1H-pyrazol-1-yl)phenoxy)phenoxy)pyridine (10 mmol), and anhydrous, degassed acetonitrile (100 mL). The solution was refluxed for 2 days, allowed to cool to room temperature, diluted with dichloromethane, and filtered through a plug of Celite. The filter cake was washed with dichloromethane (100 mL) and the filtrate was concentrated under vacuo to yield a residue, which was purified by column chromatography on silica gel to obtain the pure product 2-(3-(3-(3,5-dimethyl-1H-pyrazol-1-yl)phenoxy)phenoxy)pyridine in 45% yield. $^1$H NMR (CDCl$_3$): 2.29 (s, 3H), 2.28 (s, 3H), 5.98 (s, 1H), 6.84 (vt, 1H), 6.85-6.93 (m, 3H), 6.98-7.04 (m, 2H), 7.13 (vt, 1H), 7.19 (dd, 1H), 7.35 (vt, 1H), 7.39 (vt, 1H), 7.69 (dd, 1H), 8.19 (dd, 1H).

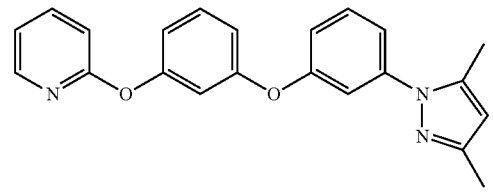

2-(3-(3-(3,5-dimethyl-1H-pyrazol-1-yl)phenoxy)phenoxy)pyridine

In another step, the Pt-001 complex was synthesized. A mixture of 2-(3-(3-(3,5-dimethyl-1H-pyrazol-1-yl)phenoxy)phenoxy)pyridine (1 mmol), K$_2$PtCl$_4$ (0.41 mg, 1 mmol), and acetic acid (35 mL) was refluxed for 3 days. The mixture was allowed to cool to room temperature. The resulting white complex was filtered off and washed with H$_2$O, cold MeOH, and Et$_2$O, and dried under vacuum to produce Pt-001 in 60% yield. The compound was sublimed under vacuum over a four zone gradient of 220° C.-190° C.-150° C.-110° C. and collected with a 65% yield. $^1$H NMR (CDCl$_3$): 2.23 (s, 3H), 2.70 (s, 3H), 6.09 (s, 1H), 6.93 (dd, 1H), 7.01 (vt, 1H), 7.03-7.11 (m, 3H), 7.14 (d, 1H), 7.17 (vt, 1H), 7.37 (d, 1H), 7.88 (dd, 1H), 8.80 (d, 1H).

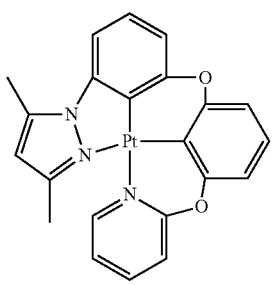

Pt-001 Complex

Example 2: Pt-008

In a second example, a Pt-008 complex, as described herein, was synthesized according to the following scheme:

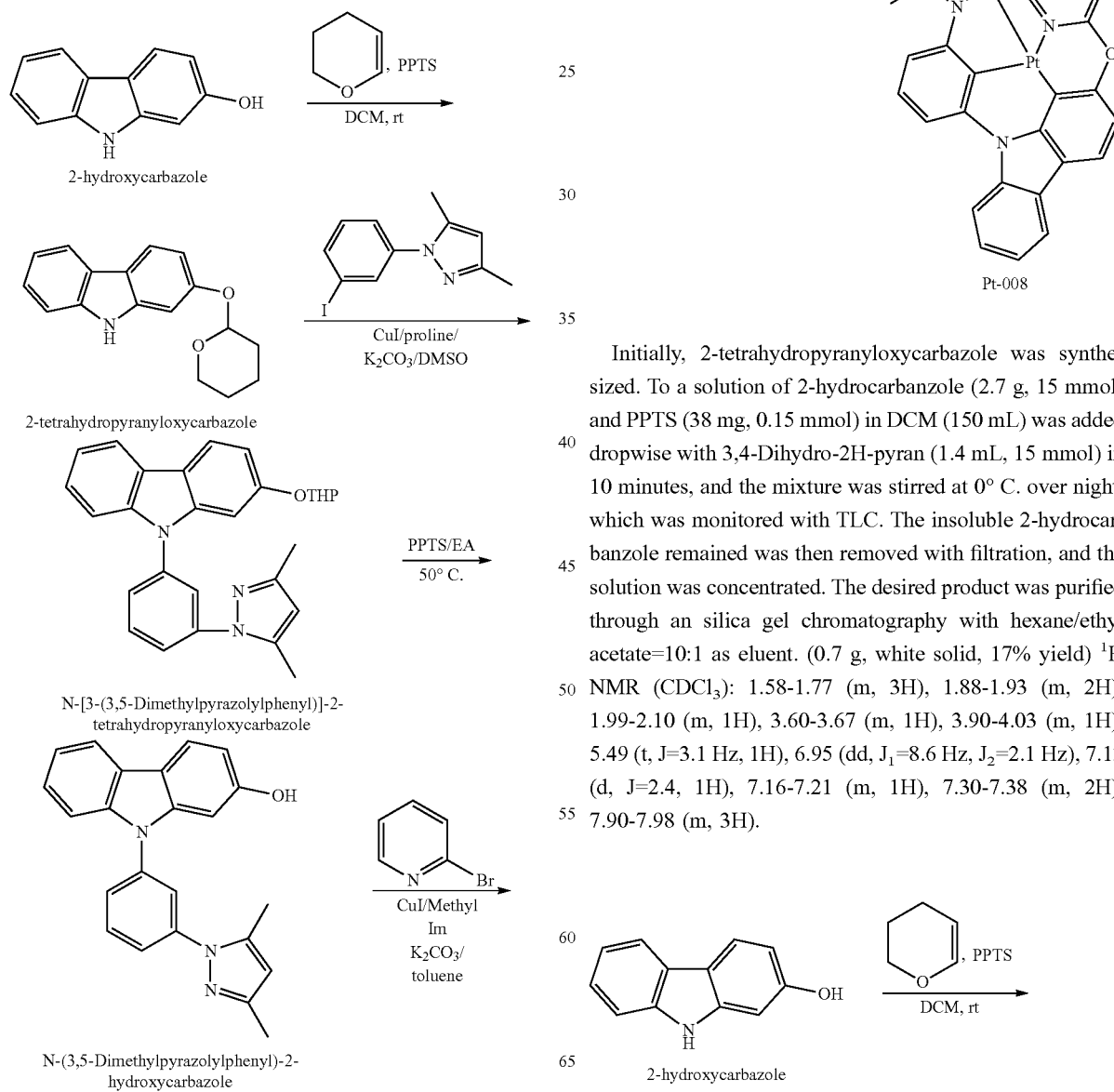

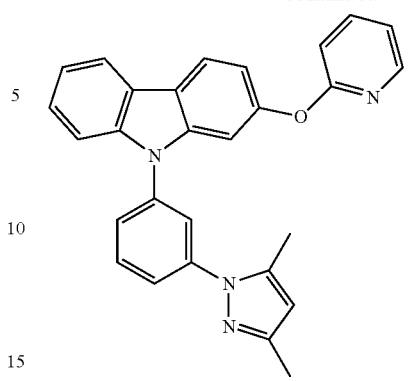

Initially, 2-tetrahydropyranyloxycarbazole was synthesized. To a solution of 2-hydrocarbanzole (2.7 g, 15 mmol) and PPTS (38 mg, 0.15 mmol) in DCM (150 mL) was added dropwise with 3,4-Dihydro-2H-pyran (1.4 mL, 15 mmol) in 10 minutes, and the mixture was stirred at 0° C. over night, which was monitored with TLC. The insoluble 2-hydrocarbanzole remained was then removed with filtration, and the solution was concentrated. The desired product was purified through an silica gel chromatography with hexane/ethyl acetate=10:1 as eluent. (0.7 g, white solid, 17% yield) $^1$H NMR (CDCl$_3$): 1.58-1.77 (m, 3H), 1.88-1.93 (m, 2H), 1.99-2.10 (m, 1H), 3.60-3.67 (m, 1H), 3.90-4.03 (m, 1H), 5.49 (t, J=3.1 Hz, 1H), 6.95 (dd, J$_1$=8.6 Hz, J$_2$=2.1 Hz), 7.13 (d, J=2.4, 1H), 7.16-7.21 (m, 1H), 7.30-7.38 (m, 2H), 7.90-7.98 (m, 3H).

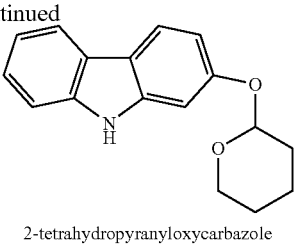

2-tetrahydropyranyloxycarbazole

In another step, N-[3-(3,5-Dimethylpyrazolylphenyl)]-2-tetrahydropyranyloxycarbazole was synthesized. To a 25 mL sealed tube was added with 2-Tetrahydropyranyloxycarbazole (380 mg, 1.42 mmol), N-(3-Iodophenyl)-3,5-dimethylpyrazole (430 mg, 1.45 mmol), potassium carbonate (415 mg, 3 mmol), copper(I) iodide (28 mg, 0.15 mmol), L-proline (35 mg, 0.3 mmol) and DMSO (5 mL) in glove box, and the mixture was stirred at 90° C. for 2 days. After cooling to rt, the mixture was treated with water (50 mL) and ethyl acetate (30 mL), and the water phase was extracted with ethyl acetate (3×20 mL). The organic extracted phase was combined, washed with brine (3×20 mL), dried with magnesium sulfate and concentrated. The resulting crud product was purified with an silica gel chromatography with hexane/ethyl acetate=5:1 as eluent to give an brown viscous solid. (460 mg, 74% yield).

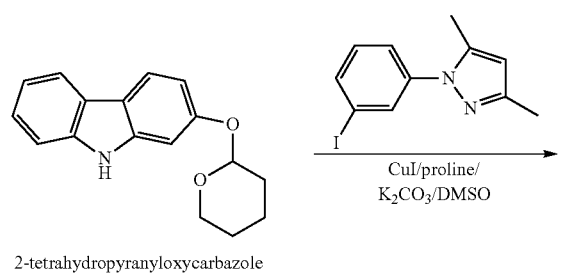

2-tetrahydropyranyloxycarbazole

N-[3-(3,5-Dimethylpyrazolylphenyl)]-2-tetrahydropyranyloxycarbazole

In another step, N-(3,5-Dimethylpyrazolylphenyl)-2-hydroxycarbazole was synthesized. To a 100 mL round flask was added with the solution of N-[3-(3,5-Dimethylpyrazolylphenyl)]-2-tetrahydropyranyloxycarbazole (330 mg, 0.75 mmol) and PPTS (1 mg) in ethyl acetate (50 mL), and the mixture was kept at 50° C. for 24 hours. After cooling, the resulting product was directly treated with an flash column using hexane/ethyl acetate=3:1 as eluent to give N-(3,5-Dimethylpyrazolyl-phenyl)-2-hydroxycarbazole as a white solid. (230 mg, 87% yield).

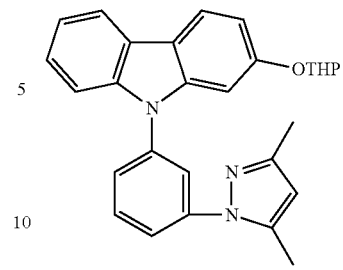

N-[3-(3,5-Dimethylpyrazolylphenyl)]-2-tetrahydropyranyloxycarbazole

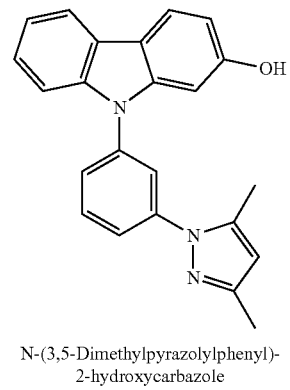

N-(3,5-Dimethylpyrazolylphenyl)-2-hydroxycarbazole

In another step, N-[3-(3,5-Dimethylpyrazolyl)phenyl]-2-(pyridinyl-2-oxy)carbazole was synthesized. To a 25 mL sealed tube in glove box was added with N-(3,5-Dimethylpyrazolylphenyl)-2-hydroxycarbazole (210 mg, 0.60 mmol), 2-bromopydine (0.1 mL, 0.9 mmol), 1-methylimidazole (24 µL, 0.9 mmol), potassium carbonate (166 mg, 1.2 mmol), copper(I) iodide (12 mg, 0.06 mmol) and toluene (2 mL), and the mixture was heated at 120° C. for 3 days. After cooling to rt, the mixture was treated with water (50 mL) and ethyl acetate (30 mL), and the water phase was extracted with ethyl acetate (3×20 mL). The organic extracted phase was combined, washed with brine (3×20 mL), dried with magnesium sulfate and concentrated. Further purification of chromatography gave the product as a clear gel solid. (0.20 g, 77% yield).

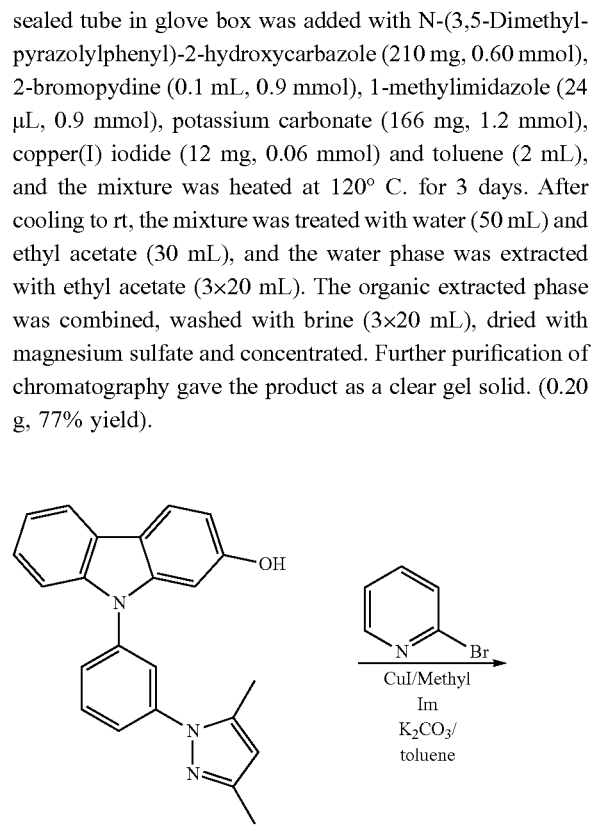

N-(3,5-Dimethylpyrazolylphenyl)-2-hydroxycarbazole

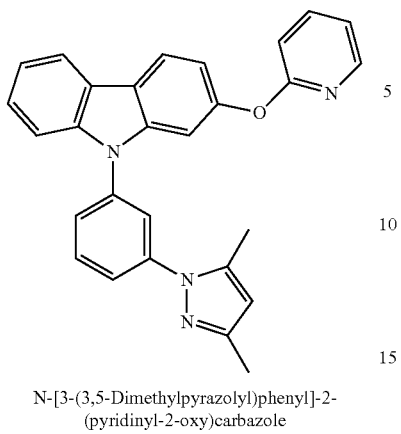

N-[3-(3,5-Dimethylpyrazolyl)phenyl]-2-
(pyridinyl-2-oxy)carbazole

In another step, the Pt-008 complex, as described herein was synthesized. To a 25 mL sealed tube in glove box was added with N-[3-(3,5-Dimethylpyrazolyl) phenyl]-2-(pyridinyl-2-oxy)carbazole (80 mg, 0.17 mmol), potassium tetrachloro-platinate (70.6 mg, 0.17 mmol) and acetic acid (3 mL), and the mixture was heated at 120° C. for 3 days after bubbled for 15 minutes. After cooling to room temperature, the resulting solution was treated with water (15 mL), and a dash solid was precipitated out. The solid was collected and purified with a flash neutral aluminum oxide column using hexane/DCM=1:1 as an eluent to give a complex as gray solid. (25 mg, 23% yield) $^1$H NMR (d$^6$-DMSO): 2.21 (s, 3H), 2.71 (s, 3H), 5.72 (s, 1H), 6.37 (s, 1H), 7.16 (d, J=12.0, 1H), 7.23-7.29 (m, 2H), 7.33-7.45 (m, 3H), 7.55 (d, J=8.0, 1H), 7.91 (d, J=8.0, 1H), 7.99 (d, J=8.0, 1H), 8.10-8.16 (m, 1H), 8.17 (d, J=8.0, 1H), 8.28 (d, J=8.0, 1H), 8.82 (d, J=5.6, 1H). The reaction was then scaled to get 100 mg Pt-008, which give 30 mg crystallized Pt-008 after sublimation.

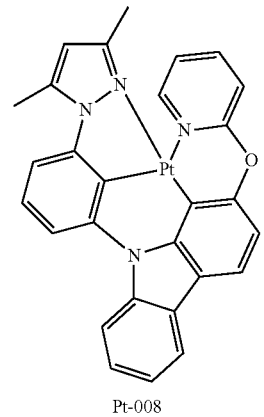

Pt-008

Example 3: Pt-009

In a third example, a Pt-009 complex, as described herein, was synthesized according to the following scheme:

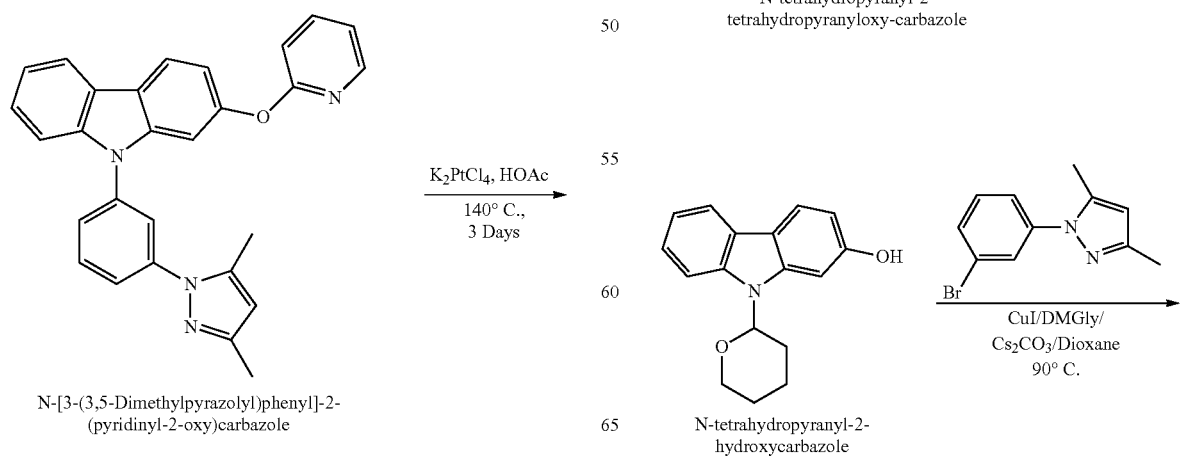

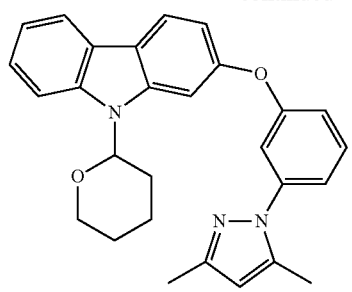

2-[3-(3,5-Dimethylpyrazol-1-yl)-phenoxy]-
N-(tetrahydropyranyl)carbazole

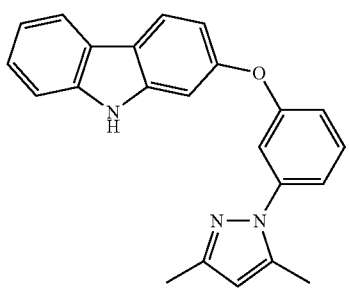

2-[3-(3,5-Dimethylpyrazol-1-yl)-phenoxy]-
carbazole

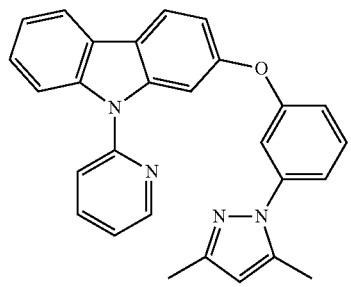

2-[3-(3,5-Dimethylpyrazol-1-yl)-
phenoxy]-9-pyridin-2-ylcarbazole

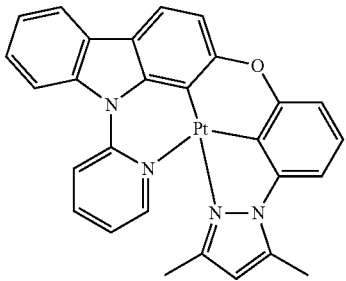

Pt-009

Initially, N-tetrahydropyranyl-2-tetrahydropyranyloxy-carbazole was synthesized. To a solution of 2-hydrocarbanzole (2.7 g, 15 mmol) and PPTS (38 mg, 0.15 mmol) in DCM (150 mL) was added dropwise with 3,4-Dihydro-2H-pyran (5 mL, 54 mmol) in 10 minutes, and the mixture was stirred at rt for 16 hours, which was monitored with TLC. The clear solution was concentrated. The desired product was purified through an silica gel chromatography with hexane/ethyl acetate=10:1 as eluent. (5.1 g, white solid, 96% yield).

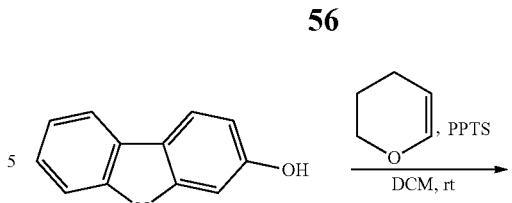

2-hydroxycarbazole

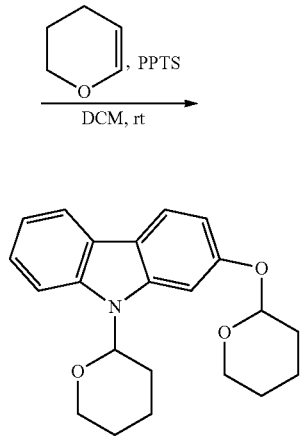

N-tetrahydropyranyl-2-
tetrahydropyranyloxy-carbazole

In another step, N-tetrahydropyranyl-2-hydroxycarbazole was synthesized. To a 250 mL round flask was added with the solution of N-tetrahydropyranyl-2-tetrahydro-pyranyloxy-carbazole (1.77 g, 5.0 mmol) and PTSA (10 mg, 0.05 mmol) in ethyl acetate (100 mL), and the mixture was kept at rt over night. TLC showed that most of the disubstituted carbazole was transferred, and trace sodium bicarbonate was slowly added into the system to quench the reaction. The volatiles ware removed in vacuum, and the resulting product was treated with an usual work-up procedure. Flashing silica gel chromatography using hexane/ethyl acetate=5:1 as eluent to give 2-[3-(3,5-Dimethylpyrazol-1-yl)-phenoxy]-carbazole as a white solid. (1.06 g, 79% yield).

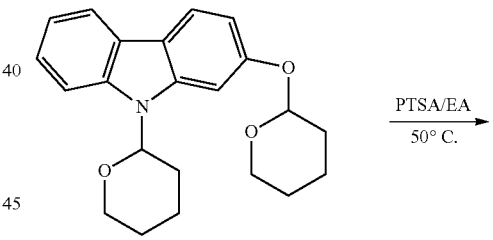

N-tetrahydropyranyl-2-
tetrahydropyranyloxy-carbazole

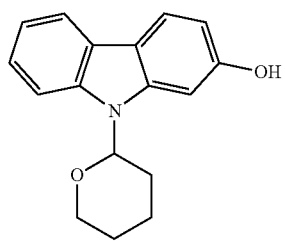

N-tetrahydropyranyl-
2-hydroxycarbazole

In another step, 2-[3-(3,5-Dimethylpyrazol-1-yl)-phenoxy]-N-(tetrahydropyranyl) carbazole was synthesized. To a 100 mL sealed tube was added with N-tetrahydropyranyl-2-hydroxycarbazole (880 mg, 3.0 mmol), N-(3-Bromophenyl)-3,5-dimethylpyrazole (826 mg, 3.30 mmol), Cesium carbonate (2.9 g, 3 mmol), copper(I) iodide (57 mg, 0.3 mmol), N, N-dimethylglycine (93 mg, 0.9 mmol) and 1,4-dioxane (8 mL) in glove box, and the mixture was stirred at 90° C. for 3 days. After cooling to rt, the mixture was treated with water (75 mL) and ethyl acetate (40 mL), and the water phase was extracted with ethyl acetate (3×30 mL). The organic extracted phase was combined, washed with brine (3×30 mL), dried with magnesium sulfate and concentrated. The resulting crude product was purified with an silica gel chromatography with hexane/ethyl acetate=3:1 as eluent to give an white colloidal solid. (1.12 g, 79% yield).

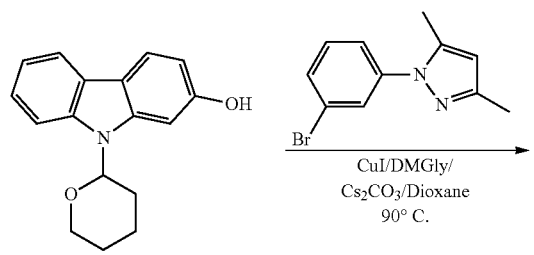

N-tetrahydropyranyl-2-hydroxycarbazole

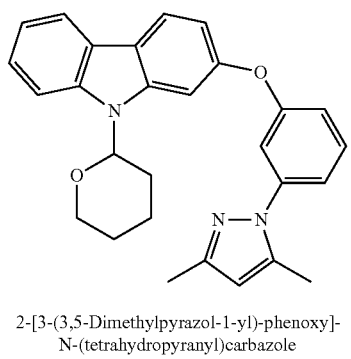

2-[3-(3,5-Dimethylpyrazol-1-yl)-phenoxy]-N-(tetrahydropyranyl)carbazole

In another step, 2-[3-(3,5-Dimethylpyrazol-1-yl)-phenoxy]-carbazole was synthesized. To a 50 mL round flask was added with the solution of 2-[3-(3,5-Dimethylpyrazol-1-yl)-phenoxy]-N-(tetrahydropyranyl)carbazole (0.49 g, 1.12 mmol) and MsOH (0.36 mL, 5.6 mmol) in methanol (20 mL), and the mixture was kept at rt for 30 minutes then 50° C. for 1.5 hours. TLC showed that all the protected starting material was transferred, and then trace sodium bicarbonate was added into the system to quench the reaction. The resulting product was directly treated with an flash column using hexane/ethyl acetate=3:1 as eluent to give N-tetrahydropyranyl-2-hydroxycarbazole as a white solid. (0.32 g, 81% yield).

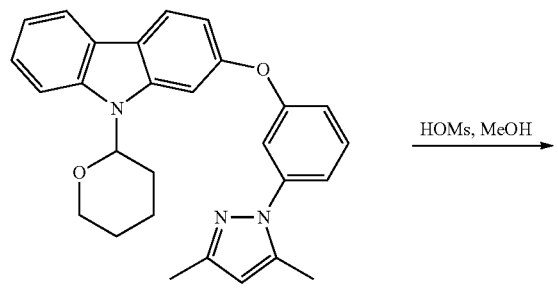

2-[3-(3,5-Dimethylpyrazol-1-yl)-phenoxy]-N-(tetrahydropyranyl)carbazole

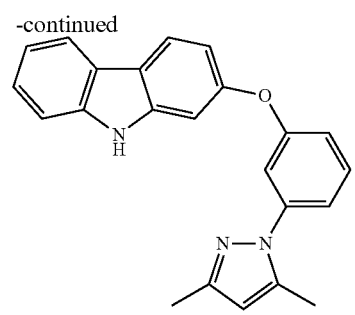

2-[3-(3,5-Dimethylpyrazol-1-yl)-phenoxy]-carbazole

In another step, 2-[3-(3,5-Dimethylpyrazol-1-yl)-phenoxy]-9-pyridin-2-ylcarbazole was synthesized. To a 25 mL sealed tube in glove box was added with 2-[3-(3,5-Dimethylpyrazol-1-yl)-phenoxy]-carbazole (450 mg, 1.27 mmol), 2-bromopydine (0.41 mL, 3.82 mmol), 1-methylimidazole (0.05 mL, 0.64 mmol), potassium carbonate (351 mg, 2.54 mmol), copper(I) iodide (25 mg, 0.13 mmol) and toluene (10 mL), and the mixture was heated at 120° C. for 3 days. After cooling to rt, the mixture was treated with water (50 mL) and ethyl acetate (30 mL), and the water phase was extracted with ethyl acetate (3×20 mL). The organic extracted phase was combined, washed with brine (3×20 mL), dried with magnesium sulfate and concentrated. The crude product was further purified with chromatography to give a clear gel solid. (520 mgg, 95% yield).

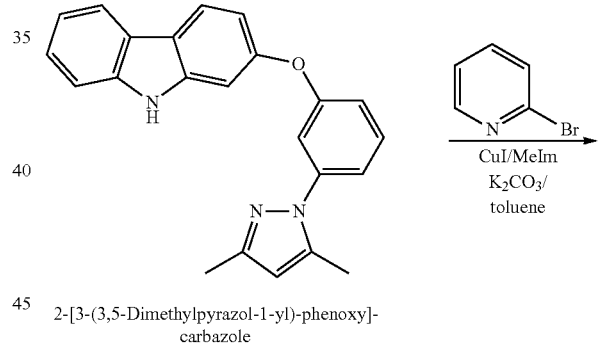

2-[3-(3,5-Dimethylpyrazol-1-yl)-phenoxy]-carbazole

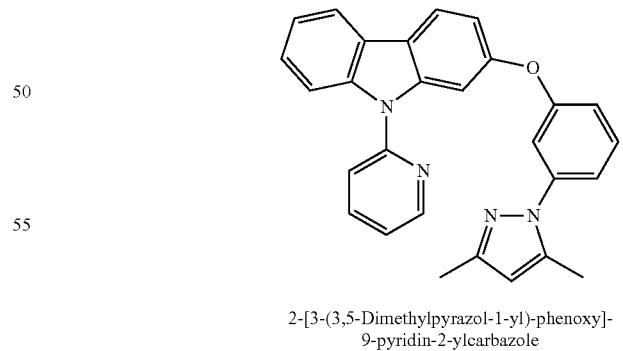

2-[3-(3,5-Dimethylpyrazol-1-yl)-phenoxy]-9-pyridin-2-ylcarbazole

In another step, the Pt-009 complex, as described herein, was synthesized. To a 100 mL sealed tube in glove box was added with 2-[3-(3,5-Dimethylpyrazol-1-yl)-phenoxy]-9-pyridin-2-ylcarbazole (520 mg, 1.21 mmol), potassium tetrachloro-platinate (552 mg, 1.33 mmol) and acetic acid (25 mL), and the mixture was heated at 110° C. for 3 days after bubbled for 15 minutes. After cooling to rt, the resulting solution was treated with water (70 mL), and a dash solid was precipitated out. The solid was collected and purified with a flash neutral aluminum oxide column using DCM as an eluent to give a complex as gray solid. (370 mg, 47% yield) Further purification by sublimation give 100 mg crystallized solid of Pt-009. $^1$H NMR (CDCl$_3$): 1.58-1.77 (m, 3H), 1.88-1.93 (m, 2H), 1.99-2.10 (m, 1H), 3.60-3.67 (m, 1H), 3.90-4.03 (m, 1H), 5.49 (t, J=3.1 Hz, 1H), 6.95 (dd, J$_1$=8.6 Hz, J$_2$=2.1 Hz), 7.13 (d, J=2.4, 1H), 7.16-7.21 (m, 1H), 7.30-7.38 (m, 2H), 7.90-7.98 (m, 3H).

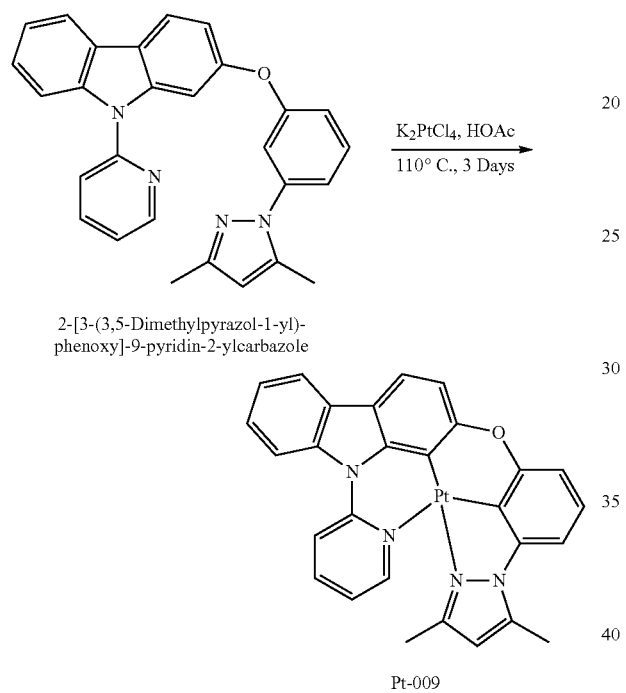

What is claimed is:

1. A compound represented by one of the following formula:

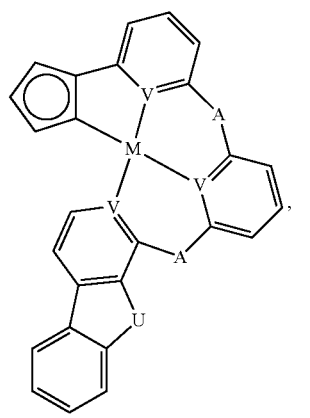

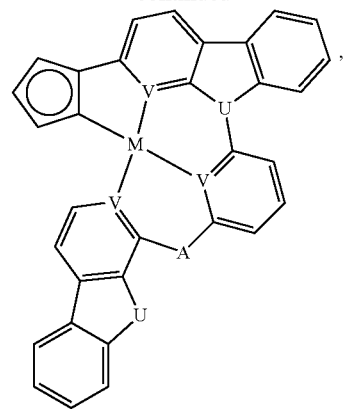

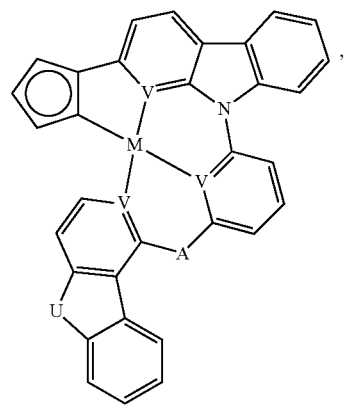

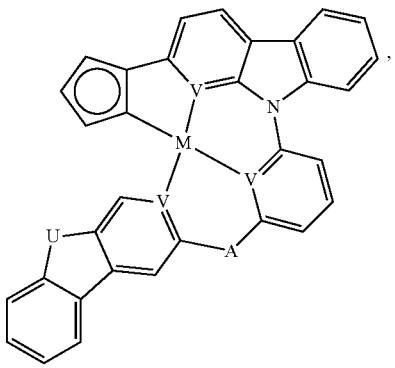

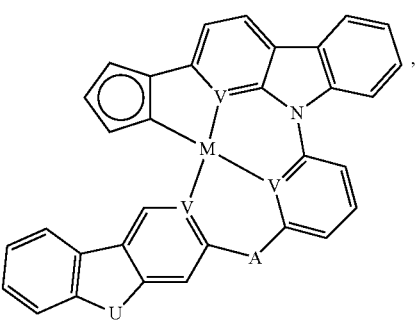

-continued

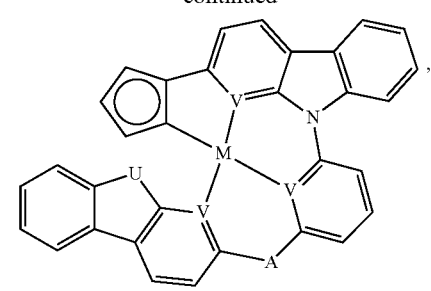

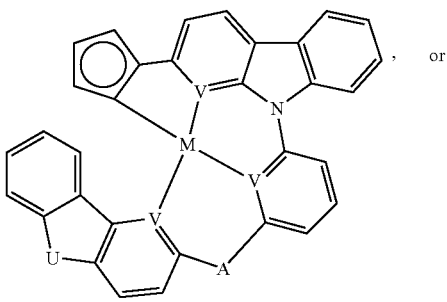

, or

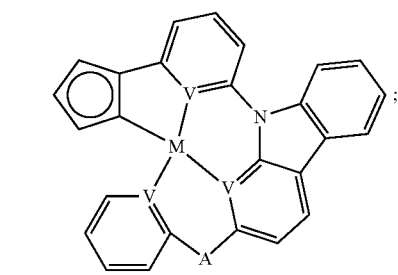

;

wherein M is platinum or palladium;

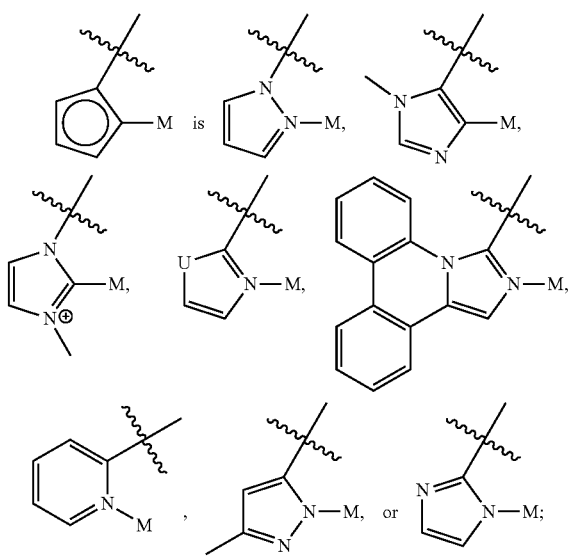

V is N or C;
U is N or a group comprising C; and
A is O, N, or a group comprising C or Si.

2. The compound of claim 1, wherein the compound is a compound of formula:

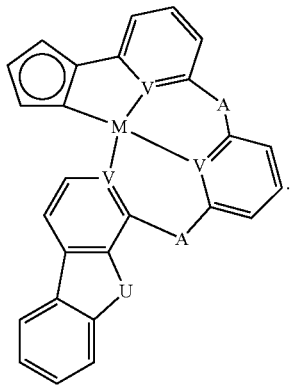

3. The compound of claim 1, wherein the compound is a compound of formula:

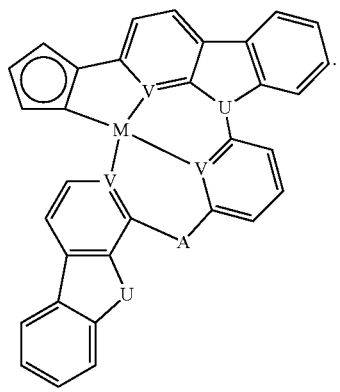

4. The compound of claim 1, wherein the compound is a compound of formula:

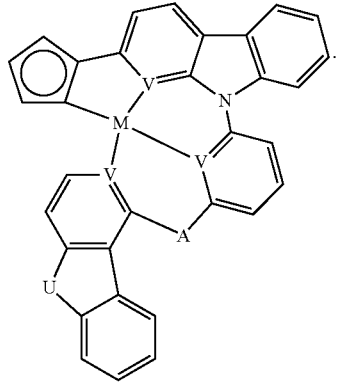

5. The compound of claim 1, wherein the compound is a compound of formula:

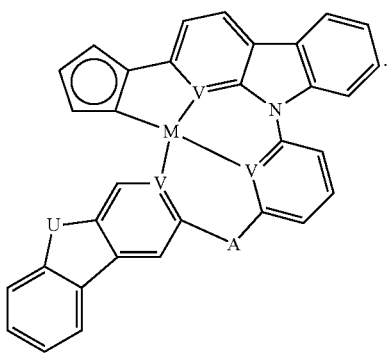

6. The compound of claim 1, wherein the compound is a compound of formula:

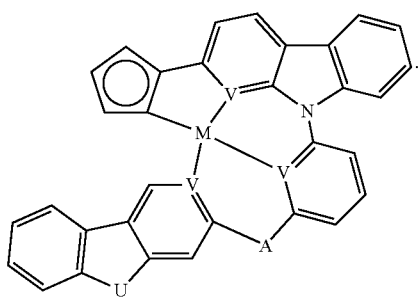

7. The compound of claim 1, wherein the compound is a compound of formula:

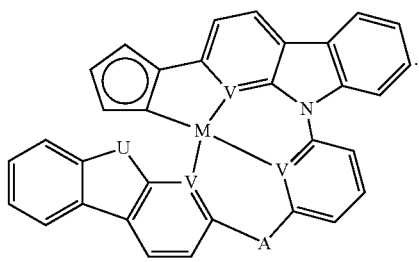

8. The compound of claim 1, wherein the compound is a compound of formula:

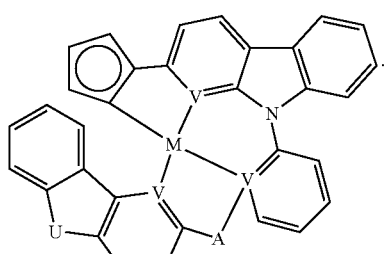

9. The compound of claim 1, wherein the compound is a compound of formula:

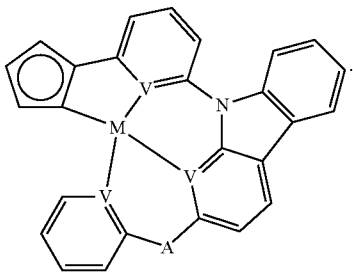

10. The compound of claim 1, wherein V is N.
11. The compound of claim 1, wherein U is N.
12. The compound of claim 1, wherein A is O.
13. The compound of claim 1, wherein

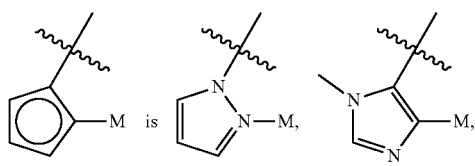

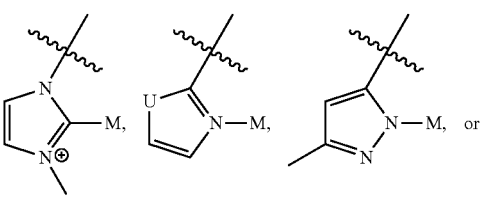

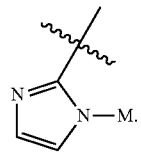

14. A light emitting device comprising the compound of claim 1.
15. An OLED device comprising the compound of claim 1.
16. The OLED device of claim 15, wherein the device is a phosphorescent OLED device.
17. A photovoltaic device comprising the compound of claim 1.

* * * * *

UNITED STATES PATENT AND TRADEMARK OFFICE
CERTIFICATE OF CORRECTION

PATENT NO. : 9,711,742 B2
APPLICATION NO. : 15/243801
DATED : July 18, 2017
INVENTOR(S) : Jian Li, Eric Turner and Xiaochun Hang Page 1 of 1

It is certified that error appears in the above-identified patent and that said Letters Patent is hereby corrected as shown below:

In the Specification

Please insert the following paragraphs at Column 1 between Lines 23 and 24:
--STATEMENT REGARDING FEDERALLY SPONSORED RESEARCH OR DEVELOPMENT
This invention was made with government support under 0748867 awarded by the National Science Foundation. The government has certain rights in the invention.--

Signed and Sealed this
Thirtieth Day of July, 2019

Andrei Iancu
*Director of the United States Patent and Trademark Office*